(12) United States Patent
Chang

(10) Patent No.: US 9,221,904 B2
(45) Date of Patent: Dec. 29, 2015

(54) TREATMENT OF OSTEOARTHRITIS USING IL-20 ANTAGONISTS

(71) Applicant: National Cheng Kung University, Tainan (TW)

(72) Inventor: Ming-Shi Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 28 days.

(21) Appl. No.: 13/945,524

(22) Filed: Jul. 18, 2013

(65) Prior Publication Data

US 2014/0023648 A1 Jan. 23, 2014

Related U.S. Application Data

(60) Provisional application No. 61/673,431, filed on Jul. 19, 2012.

(51) Int. Cl.
| | | |
|---|---|---|
| *A61K 39/395* | (2006.01) | |
| *A61K 39/00* | (2006.01) | |
| *C07K 16/24* | (2006.01) | |
| *C07K 16/28* | (2006.01) | |

(52) U.S. Cl.
CPC ........... *C07K 16/244* (2013.01); *C07K 16/2866* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,585,089 A | 12/1996 | Queen et al. | |
| 5,605,690 A | 2/1997 | Jacobs et al. | |
| 5,888,510 A | 3/1999 | Kishimoto et al. | |
| 6,835,727 B2 | 12/2004 | Okamoto et al. | |
| 7,119,191 B2 | 10/2006 | Conklin et al. | |
| 7,122,632 B2 | 10/2006 | Foster et al. | |
| 7,151,166 B2 | 12/2006 | Conklin et al. | |
| 7,189,394 B2 | 3/2007 | Thompson et al. | |
| 7,393,684 B2 | 7/2008 | Xu et al. | |
| 7,435,800 B2 | 10/2008 | Chang | |
| 7,611,705 B2 | 11/2009 | Chang | |
| 7,744,874 B2 | 6/2010 | Korytko et al. | |
| 7,786,274 B2 | 8/2010 | Chang | |
| 7,837,994 B2 | 11/2010 | Chang | |
| 7,901,684 B2 * | 3/2011 | Gill et al. .................. | 424/145.1 |
| 8,012,478 B2 | 9/2011 | Chang | |
| 8,206,712 B2 | 6/2012 | Chang | |
| 8,287,861 B2 | 10/2012 | Pass et al. | |
| 8,454,956 B2 | 6/2013 | Chang | |
| 8,597,647 B1 | 12/2013 | Chang et al. | |
| 2002/0151532 A1 | 10/2002 | Kagan et al. | |
| 2003/0148955 A1 | 8/2003 | Pluenneke | |
| 2004/0009168 A1 | 1/2004 | Kaisheva et al. | |
| 2004/0191243 A1 | 9/2004 | Chen et al. | |
| 2004/0197324 A1 | 10/2004 | Liu et al. | |
| 2004/0235728 A1 | 11/2004 | Stoch et al. | |
| 2004/0235808 A1 | 11/2004 | Wang | |
| 2005/0003475 A1 | 1/2005 | Foster et al. | |
| 2005/0136004 A1 | 6/2005 | Xu et al. | |
| 2005/0143333 A1 | 6/2005 | Richards et al. | |
| 2005/0170468 A1 | 8/2005 | Xu et al. | |
| 2006/0134756 A1 | 6/2006 | Xu et al. | |
| 2006/0142550 A1 | 6/2006 | Chang | |
| 2006/0177447 A1 | 8/2006 | Xu et al. | |
| 2006/0188476 A1 | 8/2006 | Olsen et al. | |
| 2006/0269551 A1 | 11/2006 | Thompson et al. | |
| 2007/0053871 A1 | 3/2007 | Li et al. | |
| 2007/0116700 A1 | 5/2007 | Liu et al. | |
| 2008/0247945 A1 | 10/2008 | Xu et al. | |
| 2008/0311115 A1 | 12/2008 | Chang | |
| 2009/0048432 A1 | 2/2009 | Chang | |
| 2009/0312236 A1 | 12/2009 | Beals et al. | |
| 2010/0086548 A1 | 4/2010 | Chang | |
| 2011/0002925 A1 | 1/2011 | Chang | |
| 2011/0064731 A1 | 3/2011 | Chang | |
| 2011/0091475 A1 | 4/2011 | Pass et al. | |
| 2011/0256093 A1 | 10/2011 | Chang | |
| 2011/0305698 A1 | 12/2011 | Chang | |
| 2011/0305699 A1 | 12/2011 | Chang | |
| 2013/0216534 A1 | 8/2013 | Chang | |
| 2013/0315893 A1 | 11/2013 | Chang et al. | |
| 2014/0065144 A1 | 3/2014 | Chang | |

FOREIGN PATENT DOCUMENTS

| | | |
|---|---|---|
| EP | 1 616 575 A1 | 1/2006 |
| EP | 1 719 780 A2 | 11/2006 |
| EP | 2050458 A1 | 4/2009 |
| JP | 2007-535490 A | 12/2007 |
| WO | WO 92/07584 A1 | 5/1992 |

(Continued)

OTHER PUBLICATIONS

Joint Health Monday, 2011. Johns Hopkins Bloomberg School of Public Health, http://www.jhsph.edu/news/stories/2011/healthy-monday-2011/08012011_joints.html downloaded Jan. 8, 2015 4:31:53 PM].*
Paul, Fundamental Immunology, 3r~ Edition, 1993, pp. 292-295, under the heading "Fv Structure and Diversity in Three Dimensions".*
Rudikoff et al Proc. Natl. Acad. Sci.USA, 79(6):1979-1983, Mar. 1982.*
Colman P. M. Research in Immunology, 145:33-36, 1994.*
Jorgensen et al. 2011. Osteoarthritis and Cartilage 19:1176-1182.*
[No Author Listed] Stroke. Mayo Clinic. http://www.MayoClinic.com/. Last accessed on Sep. 29, 2009.
[No Author Listed] Stroke. Treatment and Drugs. Mayo Clinic. http://www.MayoClinic.com/. Last accessed on Sep. 29, 2009. 3 pages.
Alanara et al., Expression of IL-10 family cytokines in rheumatoid arthritis: elevated levels of IL-19 in the joints. Scand J Rheumatol. Mar. 2010;39(2):118-26.

(Continued)

*Primary Examiner* — Shulamith H Shafer
(74) *Attorney, Agent, or Firm* — Wolf, Greenfield & Sacks, P.C.

(57) ABSTRACT

The present disclosure provides methods for alleviating or delaying the onset of osteoarthritis in a subject in need of the treatment using an IL-20 antagonist, which can be an antibody that blocks a signaling pathway mediated by IL-20, e.g., an anti-IL-20 antibody.

13 Claims, 8 Drawing Sheets

(56) References Cited

FOREIGN PATENT DOCUMENTS

| | | |
|---|---|---|
| WO | WO 99/03982 A1 | 1/1999 |
| WO | WO 99/27103 A1 | 6/1999 |
| WO | WO 01/46261 A1 | 6/2001 |
| WO | WO 03/051384 A1 | 6/2003 |
| WO | WO 2004/085475 A2 | 10/2004 |
| WO | WO 2005/052000 A2 | 6/2005 |
| WO | WO 2006/086396 A2 | 8/2006 |
| WO | WO 2007/081465 A2 | 7/2007 |
| WO | WO 2007/116818 A1 | 10/2007 |
| WO | WO 2008/009545 A1 | 1/2008 |
| WO | WO 2008/009645 A1 | 1/2008 |
| WO | WO 2008/016134 A1 | 2/2008 |
| WO | WO 2008/045563 A2 | 4/2008 |
| WO | WO 2008/086395 A2 | 7/2008 |
| WO | WO 2008/157161 A1 | 12/2008 |
| WO | WO 2009/077483 A1 | 6/2009 |
| WO | WO 2009/103113 A1 | 8/2009 |
| WO | WO 2010/000721 A1 | 1/2010 |
| WO | WO 2010/072691 A1 | 7/2010 |
| WO | WO 2011/104381 A2 | 9/2011 |
| WO | WO 2011/147921 A1 | 12/2011 |

OTHER PUBLICATIONS

Balmaña et al., ESMO Guidelines Working Group. BRCA in breast cancer: ESMO clinical recommendations. Ann Oncol. May 2009;20 Suppl. 4: 19-20.

Baselga, The EGFR as a target for anticancer therapy—focus on cetuximab. Eur J Cancer. Sep. 2001;37 Suppl 4:S16-22.

Beiboer et al., Guided selection of a pan carcinoma specific antibody reveals similar binding characteristics yet structural divergence between the original murine antibody and its human equivalent. J Mol Biol. Feb. 25, 2000;296(3):833-49.

Blumberg et al., Interleukin 20: discovery, receptor identification, and role in epidermal function. Cell. Jan. 12, 2001;104(1):9-19.

Body et al., A study of the biological receptor activator of nuclear factor-kappaB ligand inhibitor, denosumab, in patients with multiple myeloma or bone metastases from breast cancer. Clin Cancer Res. Feb. 15, 2006 ;12(4):1221-8.

Boyle et al., Osteoclast differentiation and activation. Nature. May 15, 2003 ;423(6937):337-42.

Chang et al., Crystal structure of interleukin-19 defines a new subfamily of helical cytokines. J Biol Chem. Jan. 31, 2003 ;278(5):3308-13. Epub Oct. 25, 2002.

Chen et al., IL-20 is regulated by hypoxia-inducible factor and upregulated after experimental ischemic stroke. J Immunol. Apr. 15, 2009;182(8):5003-12.

Chuntharapai et al., Generation of monoclonal antibodies to chemokine receptors. Methods Enzymol. 1997;288:15-27.

Cunningham et al., High-resolution epitope mapping of hGH-receptor interactions by alanine-scanning mutagenesis. Science. Jun. 2, 1989;244(4908):1081-5.

D'Andrea et al., Interleukin 10 (IL-10) inhibits human lymphocyte interferon gamma-production by suppressing natural killer cell stimulatory factor/IL-12 synthesis in accessory cells. J Exp Med. Sep. 1, 1993;178(3):1041-8.

Dumont, IL-10-related cellular cytokines and their receptors: new targets for inflammation and cancer therapy. Expert Opin Ther Patents. Mar. 2004;14(3):281-99.

Dumoutier et al., Cutting edge: STAT activation by IL-19, IL-20 and mda-7 through IL-20 receptor complexes of two types. J Immunol. Oct. 1, 2001;167(7):3545-9.

Egermann et al., Direct adenoviral transfer of bone morphogenetic protein-2 cDNA enhances fracture healing in osteoporotic sheep. Hum Gene Ther. May 2006;17(5):507-17.

EST From Incyte Pharmaceuticals Inc., INC819592. 1996. 1 page.

Fox et al. Breast tumor angiogenesis. Breast Cancer Resear. Dec. 18, 2007;9(216):1-11.

Fox et al., Loss of bone density and lean body mass after hip fracture. Osteoporos Int. 2000;11(1):31-5.

GenBank Accession No. AAK84423.1, last updated Aug. 9, 2001, located at http://www.ncbi.nlm.nih.gov/protein/15128211, last visited on Jan. 14, 2010, one page.

George et al., Current Methods in Sequence Comparison. Macromolecular Sequencing and Synthesis. 1988;127-49.

Goffe et al., Etanercept: An overview. J Am Acad Dermatol. Aug. 2003;49(2 Suppl):S105-11.

Harlow et al., Antibodies A Laboratory Manual. Cold Springs Harbor Laboratory. 1988;76.

Holliger et al., "Diabodies"• small bivalent and bispecific antibody fragments. Proc Natl Acad Sci U S A. Jul. 15, 1993;90(14):6444-8.

Hor et al., The T-cell lymphokine interleukin-26 targets epithelial cells through the interleukin-20 receptor 1 and interleukin-10 receptor 2 chains. J Biol Chem. Aug. 6, 2004;279(32):33343-51. Epub Jun. 3, 2004.

Hsieh et al., Interleukin-20 promotes angiogenesis in a direct and indirect manner Genes Immun. Apr. 2006;7(3): 234-52.

Hsing et al., The distribution of interleukin-19 in healthy and neoplastic tissue. Cytokine. Nov. 2008;44(2):221-8. Epub Sep. 21, 2008.

Hsu et al., Anti-IL-20 monoclonal antibody inhibits the differentiation of osteoclasts and protects against osteoporotic bone loss. J Exp Med. Aug. 29, 2011;208(9):1849-61. Epub Aug. 15, 2011.

Hsu et al., Function of interleukin-20 as a proinflammatory molecule in rheumatoid and experimental arthritis. Arthritis Rheum. Sep. 2006;54(9):2722-33.

Hunt et al., Ultraviolet B light stimulates interleukin-20 expression by human epithelial keratinocytes. Photochem Photobiol. Sep.-Oct. 2006;82(5):1292-300.

Incyte Pharmaceuticals Inc., INC4304592, Jul. 8, 1998. 1 page.

Jung et al., Analysis of the expression profiles of cytokines and cytokine-related genes during the progression of breast cancer growth in mice. Oncol Rep. Nov. 2009;22(5):1141-7.

Kataja et al., ESMO Guidelines Working Group. Primary breast cancer: ESMO clinical recommendations for diagnosis, treatment and follow-up. Ann Oncol. May 2009;20 Suppl 4:10-4.

Klimka et al., Human anti-CD30 recombinant antibodies by guided phage antibody selection using cell panning. Br J Cancer. Jul. 2000;83(2):252-60.

Kragstrup et al., The expression of IL-20 and IL-24 and their shared receptors are increased in rheumatoid arthritis and spondyloarthropathy. Cytokine. Jan. 2008;41(1):16-23. Epub Dec. 3, 2007.

Li et al., Interleukin-20 induced cell death in renal epithelial cells and was associated with acute renal failure. Genes Immun. Jul. 2008;9(5):395-404. Epub May 22, 2008.

Lonberg, Human monoclonal antibodies from transgenic mice. Handbook Exp Pharmacol. 2008;(181):69-97.

Marie et al., Osteoblasts in osteoporosis: past, emerging, and future anabolic targets. Eur J Endocrinol. Jul. 2011;165(1):1-10. doi: 10.1530/EJE-11-0132. Epub May 4, 2011.

Mikayama et al., Molecular cloning and functional expression of a cDNA encoding glycosylation-inhibiting factor. Proc Natl Acad Sci U S A. Nov. 1, 1993;90(21):10056-60.

Nelson et al., U.S. Preventive Services Task Force. Screening for breast cancer: an update for the U.S. Preventive Services Task Force. Ann Intern Med. Nov. 17, 2009;151(10):727-37, W237-42.

Ominsky et al., Two doses of sclerostin antibody in cynomolgus monkeys increases bone formation, bone mineral density, and bone strength. J Bone Miner Res. May 2010;25(5):948-59. doi: 10.1002/jbmr.14.

Otkjaer et al., The dynamics of gene expression of interleukin-19 and interleukin-20 and their receptors in psoriasis. Br J Dermatol. Nov. 2005;153(5):911-8.

Parrish-Novak et al., Interleukins 19, 20, and 24 signal through two distinct receptor complexes. Differences in receptor-ligand interactions mediate unique biological functions. J Biol Chem. Dec. 6, 2002;277(49):47517-23. Epub Sep. 25, 2002.

Parrish-Novak et al., Overlapping Ligand Specificities but Divergent Function in the IL-20 Sub family. J Interferon Cytokine Res. 2002;22. Supplement 46.

(56) References Cited

OTHER PUBLICATIONS

Recker et al., The effect of antiresorptives on bone quality. Clin Orthop Relat Res. Aug. 2011;469(8):2207-14. doi: 10.1007/s11999-011-1909-8.
Rich, IL-20: a new target for the treatment of inflammatory skin disease. Expert Opin Ther Targets. Apr. 2003;7(2):165-74.
Rodan et al., Therapeutic approaches to bone diseases. Science. Sep. 1, 2000;289(5484):1508-14.
Rohovsky et al., Growth Factors and Angiogenesis in Wound Healing. Growth Factors Wound Healing. Ziegler et al., eds. 1997:8-26.
Romer et al., Epidermal overexpression of interleukin-19 and -20 mRNA in psoriatic skin disappears after short-term treatment with cyclosporine a or calcipotriol. J Invest Dermatol. Dec. 2003;121(6):1306-11.
Sabat et al., IL-19 and IL-20:two novel cytokines with importance in inflammatory diseases. Expert Opinion Therapeutic Targets. May 2007;11(5):p601-12. Abstract Only.
Saidenberg-Kermanac'H et al., TNF-alpha antibodies and osteoprotegerin decrease systemic bone loss associated with inflammation through distinct mechanisms in collagen-induced arthritis. Bone. Nov. 2004;35(5):1200-7.
Sakurai et al., Expression of IL-19 and its receptors in RA: potential role for synovial hyperplasia formation. Rheumatology (Oxford). Jun. 2008;47(6):815-20. Epub Apr. 8, 2008.
Salinas et al., Understanding and modulating opalescence and viscosity in a monoclonal antibody formulation. J Pharm Sci. Jan. 2010;99(1):82-93.
Seriolo et al., Bone metabolism changes during anti-TNF-alpha therapy in patients with active rheumatoid arthritis. Ann N Y Acad Sci. Jun. 2006;1069:420-7.
Siderov et al., Care with intrathecal trastuzumab. Lancet Oncology. 2006;7(11):888.
Slavin, Cytokines and Tissue Repair. J Immunol Immunopharmacol. 1997;17(1):25-9.
Staelens et al., Humanization by variable domain resurfacing and grafting on a human IgG4, using a new approach for determination of non-human like surface accessible framework residues based on homology modelling of variable domains. Mol Immunol. Mar. 2006;43(8):1243-57. Epub Aug. 22, 2005.
Stenderup et al., Interleukin 20 Controls Psoriasis Induction and Maintenance. British Journal of Dermatology. 2006;154:11-35.
Stenderup et al., Interleukin-20 plays a critical role in maintenance and development of psoriasis in the human xenograft transplantation model. Br J Dermatol. Feb. 2009;160(2):284-96. Epub Oct. 20, 2008.
Sugerman et al., Current concepts in oral cancer. Aust Dent J. 1999;44(3):147-56.
Teitelbaum, Bone resorption by osteoclasts. Science. Sep. 1, 2000;289(5484):1504-8.
Voet et al., Biochemistry. John Wiley & Sons, Inc. New York. 1990:126-8, 228-34.
Wang et al., Prominent production of IL-20 by CD68+/CD11c+ myeloid-derived cells in psoriasis: Gene regulation and cellular effects. J Invest Dermatol. Jul. 2006;126(7):1590-9. Epub Apr. 27, 2006.
Wei et al., Detection of IL-20 and its receptors on psoriatic skin. Clin Immunol. Oct. 2005;117(1): 65-72.
Wei et al., IL-20: biological functions and clinical implications. J Biomed Sci. Sep. 2006;13(5):601-12. Epub May 16, 2006.
Williams et al., Tumor angiogenesis as a prognostic factor in oral cavity tumors. Am J Surg. Nov. 1994;168(5):373-80.
Wuyts et al., Isolation of the CXC chemokines ENA-78, GRO alpha and GRO gamma from tumor cells and leukocytes reveals NH2-terminal heterogeneity. Functional comparison of different natural isoforms. Eur J Biochem. Mar. 1999;260(2):421-9.
Zheng et al., Human interleukin 24 (MDA-7/IL-24) protein kills breast cancer cells via the IL-20 receptor and is antagonized by IL-10. Cancer Immunol Immunother. Feb. 2007;56(2):205-15. Epub May 19, 2006.
Zheng et al., Role of cytokine therapy in the treatment of psoriasis. Drug Discov Today: Ther Strat. 2007;4(1):25-31.
Einhorn, Can an anti-fracture agent heal fractures? Clin Cases Miner Bone Metab. Jan. 2010; 6(3):251-4.
Xue et al., Do bisphosphonates affect bone healing? A meta-analysis of randomized controlled trials. J Orthop Surg Res. Jun. 5, 2014;9:45. doi: 10.1186/1749-799X-9-45.

\* cited by examiner

A.

B.

A.

B.

A.

B.

A.

B.

C.

```
SEQUENCE LISTING

<160> NUMBER OF SEQ ID NOS: 21

<210> SEQ ID NO 1
<211> LENGTH: 363
<212> TYPE: DNA
<213> ORGANISM: Artificial Sequence
<220> FEATURE:
<223> OTHER INFORMATION: Synthetic Polynucleotide

<400> SEQUENCE: 1
gaattgaagc ttgaggagtc tggaggaggc ttggtgcagc ctggaggatc catgaaactc        60
tcttgtgctg cctctggatt cactttagt gacgcctgga tggactgggt ccgccagtct       120
ccagagaagg ggcttgagtg gattgctgaa attagaagca aagctaataa ttatgcaaca       180
tactttgctg agtctgtgaa agggaggttc accatctcaa gagatgattc caaaagtggt       240
gtctacctgc aaatgaacaa cttaagagct gaggacactg gcatttattt ctgtaccaag       300
ttatcactac gttactggtt cttcgatgtc tggggcgcag ggaccacggt caccgtctcc       360
tca                                                                    363

<210> SEQ ID NO 2
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 2

Glu Leu Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Ile
        35                  40                  45

Ala Glu Ile Arg Ser Lys Ala Asn Asn Tyr Ala Thr Tyr Phe Ala Glu
    50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Arg Ala Glu Asp Thr Gly Ile Tyr
                85                  90                  95
```

Phe Cys Thr Lys Leu Ser Leu Arg Tyr Trp Phe Phe Asp Val Trp Gly
            100                 105                 110

Ala Gly Thr Thr Val Thr Val Ser Ser
        115                 120

<210> SEQ ID NO 3
<211> LENGTH: 339
<212> TYPE: DNA
<213> ORGANISM: Artificial Sequence
<220> FEATURE:
<223> OTHER INFORMATION: Synthetic Polynucleotide

<400> SEQUENCE: 3
gattttgtga tgacccagac tccactcact ttgtcggtta ccattggaca accagcctcc      60
atctcttgca gtcaagtca gagcctcttg gatagtgatg gaaagacata tttgaattgg     120
ttgttacaga ggccaggcca gtctccaaag cacctcatct atctggtgtc taaactggac     180
tctggagtcc ctgacaggtt cactggcagt ggatcaggga ccgatttcac actgagaatc     240
agcagagtgg aggctgagga tttgggagtt tattattgct ggcaaagtac acattttccg     300
tggacgttcg gtggaggcac caagctggaa atcaaacgg                            339

<210> SEQ ID NO 4
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 4

Asp Phe Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys His Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Tyr Cys Trp Gln Ser
                85                  90                  95

Thr His Phe Pro Trp Thr Phe Gly Gly Gly Thr Lys Leu Glu Ile Lys
            100                 105                 110

Arg

<210> SEQ ID NO 5
<211> LENGTH: 420
<212> TYPE: DNA
<213> ORGANISM: Artificial Sequence
<220> FEATURE:
<223> OTHER INFORMATION: Synthetic Polynucleotide

<400> SEQUENCE: 5
atgtacttgg gactgaacta tgttttcatc gttttttctcc tgaatggtgt ccagagtgaa      60
gtgcagcttg tggagtctgg aggaggcttg gtgcagcctg aggatccct gaaactctct     120 tgtgctgcct ctggattcac ttttagtgac gcctggatgg actgggtccg ccaggcttcc     180
gggaaggggc ttgagtggat tgctgaaatt agaagcaaag ctaataatta tgcaacatac     240

```
tttgctgagt ctgtgaaagg gaggttcacc atctcaagag atgattccaa aaacaccgcc    300
tacctgcaaa tgaacagctt aaaaaccgag gacactgccg tttattactg taccaagtta    360
tcactgcgtt actggttctt cgatgtctgg ggccagggga ccctggtcac cgtctcctca    420
```

```
<210> SEQ ID NO 6
<211> LENGTH: 140
<212> TYPE: PRT
<213> ORGANISM: Artificial Sequence
<220> FEATURE:
<223> OTHER INFORMATION: Synthetic Polypeptide

<400> SEQUENCE: 6

Met Tyr Leu Gly Leu Asn Tyr Val Phe Ile Val Phe Leu Leu Asn Gly
1               5                   10                  15

Val Gln Ser Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Asp Ala Trp Met Asp Trp Val Arg Gln Ala Ser Gly Lys Gly Leu
    50                  55                  60

Glu Trp Ile Ala Glu Ile Arg Ser Lys Ala Asn Asn Tyr Ala Thr Tyr
65                  70                  75                  80

Phe Ala Glu Ser Val Lys Gly Arg Phe Thr Ile Ser Arg Asp Asp Ser
                85                  90                  95

Lys Asn Thr Ala Tyr Leu Gln Met Asn Ser Leu Lys Thr Glu Asp Thr
            100                 105                 110

Ala Val Tyr Tyr Cys Thr Lys Leu Ser Leu Arg Tyr Trp Phe Phe Asp
        115                 120                 125

Val Trp Gly Gln Gly Thr Leu Val Thr Val Ser Ser
    130                 135                 140

<210> SEQ ID NO 7
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ala
            20                  25                  30

Trp Met Asp Trp Val Arg Gln Ala Ser Gly Lys Gly Leu Glu Trp Ile
        35                  40                  45

Ala Glu Ile Arg Ser Lys Ala Asn Asn Tyr Ala Thr Tyr Phe Ala Glu
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Lys Leu Ser Leu Arg Tyr Trp Phe Phe Asp Val Trp Gly
            100                 105                 110

Gln Gly Thr Leu Val Thr Val Ser Ser
        115                 120

<210> SEQ ID NO 8
```

<211> LENGTH: 363
<212> TYPE: DNA
<213> ORGANISM: Artificial Sequence
<220> FEATURE:
<223> OTHER INFORMATION: Synthetic Polynucleotide

<400> SEQUENCE: 8

```
gaagtgcagc ttgtggagtc tggaggaggc ttggtgcagc ctggaggatc cctgaaactc      60
tcttgtgctg cctctggatt cacttttagt gacgcctgga tggactgggt ccgccaggct     120
tccgggaagg ggcttgagtg gattgctgaa attagaagca aagctaataa ttatgcaaca     180
tactttgctg agtctgtgaa agggaggttc accatctcaa gagatgattc aaaaacacc      240
gcctacctgc aaatgaacag cttaaaaacc gaggacactg ccgtttatta ctgtaccaag     300
ttatcactgc gttactggtt cttcgatgtc tggggccagg ggaccctggt caccgtctcc     360
tca                                                                   363
```

<210> SEQ ID NO 9
<211> LENGTH: 396
<212> TYPE: DNA
<213> ORGANISM: Artificial Sequence
<220> FEATURE:
<223> OTHER INFORMATION: Synthetic Polynucleotide

<400> SEQUENCE: 9

```
atgatgagtc ctgcccagtt cctgtttctg ttggtgctct ggattcggga aaccaacggt      60
gatatcgtga tgacccagac tccactctct ttgtccgtta cccctggaca accagcctcc     120
atctcttgca gtcaagtca gagcctcttg gatagtgatg gaaagacata tttgaattgg      180
ttgttacaga agccaggcca gtctccacag cacctcatct atctggtgtc taaactggac     240
tctggagtcc ctgacaggtt cagtggcagt ggatcaggga ccgatttcac actgaaaatc     300
agcagagtgg aggctgagga tgttggagtt tattattgct ggcaaagtac acatttcccc     360
tggaccttcg gtggaggcac caaggtggaa atcaaa                              396
```

<210> SEQ ID NO 10
<211> LENGTH: 132
<212> TYPE: PRT
<213> ORGANISM: Artificial Sequence
<220> FEATURE:
<223> OTHER INFORMATION: Synthetic Polypeptide

<400> SEQUENCE: 10

```
Met Met Ser Pro Ala Gln Phe Leu Phe Leu Leu Val Leu Trp Ile Arg
1               5                   10                  15

Glu Thr Asn Gly Asp Ile Val Met Thr Gln Thr Pro Leu Ser Leu Ser
            20                  25                  30

Val Thr Pro Gly Gln Pro Ala Ser Ile Ser Cys Lys Ser Gln Ser
        35                  40                  45

Leu Leu Asp Ser Asp Gly Lys Thr Tyr Leu Asn Trp Leu Leu Gln Lys
    50                  55                  60

Pro Gly Gln Ser Pro Gln His Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Ser Thr His Phe Pro Trp Thr Phe Gly Gly Gly Thr Lys
        115                 120                 125
```

Val Glu Ile Lys
    130

<210> SEQ ID NO 11
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 11

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln His Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Ser
                85                  90                  95

Thr His Phe Pro Trp Thr Phe Gly Gly Gly Thr Lys Val Glu Ile Lys
            100                 105                 110

<210> SEQ ID NO 12
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 12
gatatcgtga tgacccagac tccactctct ttgtccgtta cccctggaca accagcctcc     60
atctcttgca agtcaagtca gagcctcttg gatagtgatg gaaagacata tttgaattgg    120
ttgttacaga agccaggcca gtctccacag cacctcatct atctggtgtc taaactggac    180
tctggagtcc ctgacaggtt cagtggcagt ggatcaggga ccgatttcac actgaaaatc    240
agcagagtgg aggctgagga tgttggagtt tattattgct ggcaaagtac acattttccc    300
tggaccttcg gtggaggcac caaggtggaa atcaaa                              336

<210> SEQ ID NO 13
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 13

Asp Phe Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln His Leu Ile Tyr Leu Val Ser Lys Leu Asp Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Ser
                 85                  90                  95

Thr His Phe Pro Trp Thr Phe Gly Gly Gly Thr Lys Val Glu Ile Lys
            100                 105                 110

<210> SEQ ID NO 14
<211> LENGTH: 457
<212> TYPE: PRT
<213> ORGANISM: Artificial Sequence
<220> FEATURE:
<223> OTHER INFORMATION: Synthetic Polypeptide

<400> SEQUENCE: 14

Met Arg Val Leu Ile Leu Leu Trp Leu Phe Thr Ala Phe Pro Gly Ile
 1               5                  10                  15

Leu Ser Val Val Gln Leu Gln Glu Ser Gly Pro Gly Leu Val Lys Pro
                 20                  25                  30

Ser Gln Ser Leu Ser Leu Thr Cys Thr Val Thr Gly Tyr Ser Ile Thr
             35                  40                  45

Ser Asp Tyr Ala Trp Asn Trp Ile Arg Gln Phe Pro Gly Asn Arg Leu
 50                  55                  60

Glu Trp Met Gly Tyr Ile Asp Tyr Ser Gly Ser Thr Lys Tyr Asn Pro
 65                  70                  75                  80

Ser Leu Lys Ser Arg Ile Ser Val Thr Arg Asp Thr Ser Lys Asn Gln
                 85                  90                  95

Phe Phe Leu Gln Leu Asn Ser Val Thr Thr Glu Asp Thr Ala Thr Tyr
            100                 105                 110

Tyr Cys Ala Arg Asp Phe Gly Asp Ala Tyr Trp Gly Gln Gly Thr Leu
        115                 120                 125

Val Thr Val Ser Ala Ala Lys Thr Thr Pro Pro Ser Val Tyr Pro Leu
130                 135                 140

Ala Pro Gly Ser Ala Ala Gln Thr Asn Ser Met Val Thr Leu Gly Cys
145                 150                 155                 160

Leu Val Lys Gly Tyr Phe Pro Glu Pro Val Thr Val Thr Trp Asn Ser
                165                 170                 175

Gly Ser Leu Ser Ser Gly Val His Thr Phe Pro Ala Val Leu Gln Ser
            180                 185                 190

Asp Leu Tyr Thr Leu Ser Ser Ser Val Thr Val Pro Ser Ser Thr Trp
        195                 200                 205

Pro Ser Glu Thr Val Thr Cys Asn Val Ala His Pro Ala Ser Ser Thr
210                 215                 220

Lys Val Asp Lys Lys Ile Val Pro Arg Asp Cys Gly Cys Lys Pro Cys
225                 230                 235                 240

Ile Cys Thr Val Pro Glu Val Ser Ser Val Phe Ile Phe Pro Pro Lys
                245                 250                 255

Pro Lys Asp Val Leu Thr Ile Thr Leu Thr Pro Lys Val Thr Cys Val
            260                 265                 270

Val Val Asp Ile Ser Lys Asp Asp Pro Glu Val Gln Phe Ser Trp Phe
        275                 280                 285

Val Asp Asp Val Glu Val His Thr Ala Gln Thr Gln Pro Arg Glu Glu
290                 295                 300

Gln Phe Asn Ser Thr Phe Arg Ser Val Ser Glu Leu Pro Ile Met His
305                 310                 315                 320
```

```
Gln Asp Trp Leu Asn Gly Lys Glu Phe Lys Cys Arg Val Asn Ser Ala
            325                 330                 335

Ala Phe Pro Ala Pro Ile Glu Leu Thr Ile Ser Lys Thr Lys Gly Arg
        340                 345                 350

Pro Lys Ala Pro Gln Val Tyr Thr Ile Pro Pro Lys Glu Gln Met
    355                 360                 365

Ala Lys Asp Lys Val Ser Leu Thr Cys Met Ile Thr Asp Phe Phe Pro
370                 375                 380

Glu Asp Ile Thr Val Glu Trp Gln Trp Asn Gly Gln Pro Ala Glu Asn
385                 390                 395                 400

Tyr Lys Asn Thr Gln Pro Ile Met Asp Thr Asp Gly Ser Tyr Phe Val
            405                 410                 415

Tyr Ser Lys Leu Asn Val Gln Lys Ser Asn Trp Glu Ala Gly Asn Thr
        420                 425                 430

Phe Thr Cys Ser Val Leu His Glu Gly Leu His Asn His His Thr Glu
    435                 440                 445

Lys Ser Leu Ser His Ser Pro Gly Lys
    450                 455
```

<210> SEQ ID NO 15
<211> LENGTH: 1374
<212> TYPE: DNA
<213> ORGANISM: Artificial Sequence
<220> FEATURE:
<223> OTHER INFORMATION: Synthetic Polynucleotide

<400> SEQUENCE: 15

```
atgagagtgc tgattctttt gtggctgttc acagcctttc tggtatcct  gtctgttgtg      60 cagcttcagg agtcgggacc tggcctggtg aaaccttctc agtctctgtc cctcacctgc     120
actgtcactg gctactcaat caccagtgat tatgcctgga actggatccg gcagtttcca     180
ggaaacagac tggagtggat gggctacata gactacagtg gtagcactaa atacaacccc     240
tctctcaaaa gtcgaatctc tgtcactcga gacacatcca agaaccagtt cttcctgcag     300
ttgaattctg tgactactga ggacacagcc acatattact gtgcaagaga ctttggtgat     360
gcttactggg gccaggggac tctggtcact gtctctgcag ccaaaacgac ccccccatct     420
gtctatccac tggcccctgg atctgctgcc caaactaact ccatggtgac cctgggatgc     480
ctggtcaagg gctatttccc tgagccagtg acagtgacct ggaactctgg atccctgtcc     540
agcggtgtgc acaccttccc agctgtcctg cagtctgacc tctacactct gagcagctca     600
gtgactgtcc cctccagcac ctgggccagc gagaccgtca cctgcaacgt tgcccacccg     660
gccagcagca ccaaggtgga caagaaaatt gtgcccaggg attgtggttg taagccttgc     720
atatgtacag tccagaagt  atcatctgtc ttcatcttcc ccccaaagcc caaggatgtg     780
ctcaccatta ctctgactcc taaggtcacg tgtgttgtgg tagacatcag caaggatgat     840
cccgaggtcc agttcagctg gtttgtagat gatgtggagg tgcacacagc tcaaacgcaa     900
ccccgggagg agcagttcaa cagcactttc cgctcagtca gtgaacttcc catcatgcac     960
caggactggc tcaatggcaa ggagttcaaa tgcagggtca acagtgcagc tttcc ctgcc    1020 cccatcgaga aaccatctc  caaaaccaaa ggcagaccga aggctccaca ggtgtacacc    1080
attccacctc ccaaggagca aatggccaag ataaagtca  gtctgacctg catgataaca    1140
gacttcttcc ctgaagacat tactgtggag tggcagtgga atgggcagcc agcggagaac    1200
tacaagaaca ctcagcccat catggacaca gatggctctt acttcgtcta cagcaagctc    1260
```

```
aatgtgcaga agagcaactg ggaggcagga aatactttca cctgctctgt gttacatgag    1320
ggcctgcaca accaccatac tgagaagagc ctctcccact ctcctggtaa atga          1374

<210> SEQ ID NO 16
<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 16

Met Asp Ser Gln Ala Gln Val Leu Met Leu Leu Leu Trp Val Ser
1               5                   10                  15

Gly Ser Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Arg Asn Gln Lys Asn Tyr Leu Ala Trp Tyr Gln Leu
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240

<210> SEQ ID NO 17
<211> LENGTH: 723
<212> TYPE: DNA
<213> ORGANISM: Artificial Sequence
<220> FEATURE:
<223> OTHER INFORMATION: Synthetic Polynucleotide

<400> SEQUENCE: 17
atggattcac aggcccaggt tcttatgtta ctgctgctat gggtatctgg ttcctgtggg     60
gacattgtga tgtcacagtc tccatcctcc ctagctgtgt cagttggaga gaaggttact    120
atgagctgca agtccagtca gagccttta tatagtagga atcaaaagaa ctacttggcc     180
tggtaccagc tgaagccagg gcagtctcct aaactgctga tttactgggc atccactagg    240
gaatctgggg tccctgatcg cttcacaggc agtggatctg gacagattt cactctcacc     300
```

-continued

```
atcagcagtg tgaaggctga agacctggca gtttattact gtcagcaata ttatagctat      360
ccgctcacgt tcggtgctgg gaccaagctg gagctgaaac gggctgatgc tgcaccaact      420
gtatccatct tcccaccatc cagtgagcag ttaacatctg gaggtgcctc agtcgtgtgc      480
ttcttgaaca acttctaccc caaagacatc aatgtcaagt ggaagattga tggcagtgaa      540
cgacaaaatg gcgtcctgaa cagttggact gatcaggaca gcaagacagg cacctacagc      600
atgagcagca ccctcacgtt gaccaaggac gagtatgaac gacataacag ctataccgt       660 gaggccactc acaagacatc aacttcaccc attgtcaaga gcttcaacag gaatgagtgt      720
tag                                                                    723
```

<210> SEQ ID NO 18
<211> LENGTH: 460
<212> TYPE: PRT
<213> ORGANISM: Artificial Sequence
<220> FEATURE:
<223> OTHER INFORMATION: Synthetic Polypeptide
<400> SEQUENCE: 18

```
Met Asn Phe Gly Leu Ser Leu Ile Phe Leu Ala Leu Ile Leu Lys Gly
1               5                   10                  15

Val Gln Cys Glu Val Gln Leu Val Glu Ala Gly Gly Asp Leu Val Lys
            20                  25                  30

Pro Gly Gly Ser Leu Lys Leu Ser Cys Ala Ala Ser Gly Phe Ser Leu
        35                  40                  45

Ser Asn Tyr Gly Met Ser Trp Val Arg Gln Thr Pro Asp Lys Arg Leu
    50                  55                  60

Glu Trp Val Ala Ser Ile Ser Ser Gly Gly Arg Phe Thr Ser Tyr Pro
65                  70                  75                  80

Asp Ser Val Arg Gly Arg Phe Thr Ile Ser Arg Asp Asn Ala Lys Asn
                85                  90                  95

Thr Leu Tyr Leu Gln Met Ser Gly Leu Lys Ser Glu Asp Thr Ala Met
            100                 105                 110

Tyr Tyr Cys Ala Arg His Asp Gly Asn Gly Gly Asp Tyr Trp Gly Gln
        115                 120                 125

Gly Thr Ser Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285
```

| Ser | Trp | Phe | Val | Asp | Asp | Val | Glu | Val | His | Thr | Ala | Gln | Thr | Gln | Pro |
| | 290 | | | | 295 | | | | 300 | | | | | | |

| Arg | Glu | Glu | Gln | Phe | Asn | Ser | Thr | Phe | Arg | Ser | Val | Ser | Glu | Leu | Pro |
| 305 | | | | | 310 | | | | | 315 | | | | | 320 |

| Ile | Met | His | Gln | Asp | Trp | Leu | Asn | Gly | Lys | Glu | Phe | Lys | Cys | Arg | Val |
| | | | 325 | | | | | 330 | | | | | 335 | | |

| Asn | Ser | Ala | Ala | Phe | Pro | Ala | Pro | Ile | Glu | Lys | Thr | Ile | Ser | Lys | Thr |
| | | | 340 | | | | | 345 | | | | | 350 | | |

| Lys | Gly | Arg | Pro | Lys | Ala | Pro | Gln | Val | Tyr | Thr | Ile | Pro | Pro | Pro | Lys |
| | | 355 | | | | | 360 | | | | | 365 | | | |

| Glu | Gln | Met | Ala | Lys | Asp | Lys | Val | Ser | Leu | Thr | Cys | Met | Ile | Thr | Asp |
| | 370 | | | | | 375 | | | | | 380 | | | | |

| Phe | Phe | Pro | Glu | Asp | Ile | Thr | Val | Glu | Trp | Gln | Trp | Asn | Gly | Gln | Pro |
| 385 | | | | | 390 | | | | | 395 | | | | | 400 |

| Ala | Glu | Asn | Tyr | Lys | Asn | Thr | Gln | Pro | Ile | Met | Asp | Thr | Asp | Gly | Ser |
| | | | | 405 | | | | | 410 | | | | | 415 | |

| Tyr | Phe | Val | Tyr | Ser | Lys | Leu | Asn | Val | Gln | Lys | Ser | Asn | Trp | Glu | Ala |
| | | | 420 | | | | | 425 | | | | | 430 | | |

| Gly | Asn | Thr | Phe | Thr | Cys | Ser | Val | Leu | His | Glu | Gly | Leu | His | Asn | His |
| | | | 435 | | | | | 440 | | | | | 445 | | |

| His | Thr | Glu | Lys | Ser | Leu | Ser | His | Ser | Pro | Gly | Lys |
| | 450 | | | | | 455 | | | | | 460 |

<210> SEQ ID NO 19
<211> LENGTH: 1383
<212> TYPE: DNA
<213> ORGANISM: Artificial Sequence
<220> FEATURE:
<223> OTHER INFORMATION: Synthetic Polynucleotide

<400> SEQUENCE: 19

| atgaacttcg ggctcagcct gattttcctt gccctcattt taaaaggtgt ccagtgtgag | 60 |
| gtgcagctgg tggaggctgg gggagactta gtgaagcctg agggtccct gaaactctcc | 120 |
| tgtgcggcct ctggattcag tttgagtaac tatggcatgt cctgggttcg ccagactcca | 180 |
| gacaagaggc tggagtgggt cgcaagcatt agtagtggtg gtcgtttcac ctccatcca | 240 |
| gacagtgtga gggggcgatt caccatctcc agagacaatg ccaagaacac cctgtacctg | 300 |
| caaatgagcg gtctgaagtc tgaggacaca gccatgtatt actgtgcaag acacgacggc | 360 |
| aacggtgggg actactgggg tcaaggaacc tcagtcaccg tctcctcagc aaaaacgaca | 420 |
| cccccatctg tctatccact ggcccctgga tctgctgccc aaactaactc catggtgacc | 480 |
| ctgggatgcc tggtcaaggg ctatttccct gagccagtga cagtgacctg aactctgga | 540 |
| tccctgtcca gcggtgtgca caccttccca gctgtcctgc agtctgacct ctacactctg | 600 |
| agcagctcag tgactgtccc ctccagcacc tggcccagcg agaccgtcac ctgcaacgtt | 660 |
| gcccacccgg ccagcagcac caaggtggac aagaaaattg tgcccaggga ttgtggttgt | 720 |
| aagccttgca tatgtacagt cccagaagta tcatctgtct tcatcttccc cccaaagccc | 780 |
| aaggatgtgc tcaccattac tctgactcct aaggtcacgt gtgttgtggt agacatcagc | 840 |
| aaggatgatc ccgaggtcca gttcagctgg tttgtagatg atgtggaggt gcacacagct | 900 |
| cagacgcaac cccgggagga gcagttcaac agcactttcc gctcagtcag tgaacttccc | 960 |
| atcatgcacc aggactggct caatggcaag gagttcaaat gcagggtcaa cagtgcagct | 1020 |
| ttccctgccc ccatcgagaa aaccatctcc aaaaccaaag gcagaccgaa ggctccacag | 1080 |

```
gtgtacacca ttccacctcc caaggagcag atggccaagg ataaagtcag tctgacctgc   1140
atgataacag acttcttccc tgaagacatt actgtggagt ggcagtggaa tgggcagcca   1200
gcggagaact acaagaacac tcagcccatc atggacacag atggctctta cttcgtctac   1260
agcaagctca atgtgcagaa gagcaactgg gaggcaggaa atactttcac ctgctctgtg   1320
ttacatgagg gcctgcacaa ccaccatact gagaagagcc tctcccactc tcctggtaaa   1380
tga                                                                 1383
```

<210> SEQ ID NO 20
<211> LENGTH: 235
<212> TYPE: PRT
<213> ORGANISM: Artificial Sequence
<220> FEATURE:
<223> OTHER INFORMATION: Synthetic Polypeptide

<400> SEQUENCE: 20

```
Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Phe Pro Ala Ile
            20                  25                  30

Leu Ser Ala Ser Pro Gly Glu Lys Val Thr Met Thr Cys Arg Ala Arg
        35                  40                  45

Ser Ser Val Ser Phe Met His Trp Tyr Gln Lys Pro Gly Ser Ser
    50                  55                  60

Pro Lys Pro Trp Ile Tyr Ala Thr Ser Asn Leu Ala Ser Gly Val Pro
65                  70                  75                  80

Pro Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Tyr Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 21
<211> LENGTH: 708
<212> TYPE: DNA
<213> ORGANISM: Artificial Sequence
<220> FEATURE:
<223> OTHER INFORMATION: Synthetic Polynucleotide

<400> SEQUENCE: 21

```
atggatttc aagtgcagat tttcagcttc ctgctaatca gtgcttcagt cataatgtcc   60
```

```
agaggacaaa ttgttctctc ccagtttcca gcaatcctgt ctgcatctcc aggggagaag      120
gtcacaatga cttgcagggc caggtcaagt gtaagtttca tgcactggta ccagcagaag      180
ccaggatcct cccccaaacc ctggatttat gccacatcca acctggcttc tggagtccct      240
cctcgcttca gtggcagtgg gtctgggacc tcttactctc tcacaatcag cagagtggag      300
gctgaagatg ctgccactta ttactgccag cagtggagta gtaacccata cacgttcgga      360
ggggggacta agctggaaat aaaacgggct gatgctgcac caactgtatc catcttccca      420
ccatccagtg agcagttaac atctggaggt gcctcagtcg tgtgcttctt gaacaacttc      480 tacccccaaag acatcaatgt caagtggaag attgatggca gtgaacgaca aaatggcgtc     540
ctgaacagtt ggactgatca ggacagcaaa gacagcacct acagcatgag cagcaccctc      600
acgttgacca aggacgagta tgaacgacat aacagctata cctgtgaggc cactcacaag      660
acatcaactt cacccattgt caagagcttc aacaggaatg agtgttag                   708
```

TREATMENT OF OSTEOARTHRITIS USING IL-20 ANTAGONISTS

RELATED APPLICATION

This application claims the benefit of U.S. provisional application No. 61/673,431, filed Jul. 19, 2012 under 35 U.S.C. §119, the entire content of which is incorporated herein by reference.

BACKGROUND OF THE INVENTION

Osteoarthritis, also known as degenerative arthritis or degenerative joint disease, is the most common form of arthritis, affecting millions of people around the world. It is characterized by cartilage breakdown, subchondral sclerosis, osteophyte formation, and alterations to the joint capsule, resulting in degradation of the joints. Osteoarthritis is age-related. Physician-diagnosed arthritis occurs in more than 50% of adults older than age 65 years and in more than 30% of adults aged 45-64 years. Valdes et al., Best practice & Research Clinical Rheumatology, 24(1):3-14; 2010.

Interleukin IL-20 (IL-20) is a member of the IL-10 family, which includes IL-10, IL-19, IL-20, IL-22, IL-24, and IL-26. Blumberg, et al., 2001, Cell 104:9-19; Pestka et al., 2004, Annu Rev Immunol 22:929-979. IL-20 is expressed in monocytes, epithelial cells, and endothelial cells and acts on multiple cell types by activating a heterodimer receptor complex of either IL-20R1/IL-20R2 or IL-22R1/IL-20R2. Dumoutier, et al., 2001, J Immunol 167:3545-3549). IL-20 was found to be involved in various inflammatory diseases, such as psoriasis (Blumberg et al., 2001; Sa et al., 2007, J Immunol 178: 2229-2240; and Wei et al., 2005, Clin Immunol 117:65-72), rheumatoid arthritis (Hsu, et al., 2006, Arthritis Rheum 54:2722-2733), atherosclerosis (Caligiuri, et al. 2006, Arterioscler Thromb Vasc Biol 26:1929-1930; and Chen et al., 2006, Arterioscler Thromb Vasc Biol 26:2090-2095), ischemic stroke (Chen et al., 2009, J Immunol 182:5003-5012), and renal failure (Li et al., 2008, Genes Immun 9:395-404). See also Wei et al., 2006, J Biomed Sci 13:601-612.

SUMMARY OF THE INVENTION

The present disclosure is based on the unexpected discoveries that IL-20 was found to be involved in the pathogenesis of osteoarthritis and that an anti-IL-20 antibody successfully alleviated disease severity in a rat osteoarthritis model. These unexpected discoveries indicate that IL-20 antagonists such as anti-IL-20 antibodies can be effective in treating osteoarthritis.

Accordingly, one aspect of the present disclosure relates to a method for alleviating or delaying the onset of osteoarthritis in a subject, the method comprising administering to a subject in need thereof an effective amount of an IL-20 antagonist, which can be an antibody that inhibits a signaling pathway mediated by IL-20.

In some embodiments, such an antibody is an antibody that binds IL-20, particularly human IL-20, and inhibits its biological activity. In one example, the anti-IL-20 antibody is monoclonal antibody mAb7E, an antigen-binding fragment thereof, or a functional variant thereof. A functional variant of mAb 7E can comprise the same complementary determining regions (CDRs) as mAb7E. In one example, the functional variant is a humanized antibody of mAb7E, e.g., a humanized antibody comprising a heavy chain variable region ($V_H$), which comprises the amino acid sequence of SEQ ID NO:7, and a light chain variable region ($V_L$), which comprises the amino acid sequence of SEQ ID NO:11 or SEQ ID NO:13.

In other embodiments, the antibody that inhibits a signaling pathway mediated by IL-20 is an antibody that binds a human IL-20 receptor (IL-20R) and inhibits the signaling pathway triggered by IL-20. The anti-IL-20R antibody can bind to one of the subunits of IL-20R such as R1. Examples of anti-IL-20R1 antibodies include, but are not limited to, antibodies comprising the same $V_H$ and $V_L$ chain as monoclonal antibody mAb51D or mAb7GW, or a functional variant thereof, which can be antibodies comprises the same complementary determining regions (CDRs) as mAb51D or mAb7GW and/or humanized antibodies of mAb51D or mAb7GW.

Any of the antibodies described herein can be a full-length antibody or an antigen-binding fragment thereof. It also can be a human antibody, a humanized antibody, a chimeric antibody, or a single-chain antibody.

The subject to be treated by the methods described herein can be a human patient having or being suspected of having osteoarthritis. Such a human patient can be 45 or older (e.g., 65 or older).

Also described herein are (a) pharmaceutical compositions for use in alleviating osteoarthritis or delaying the onset of the disease, the compositions comprising one or more of the IL-20 antagonists described herein such as anti-IL-20 and/or anti-IL-20R antibodies and a pharmaceutically acceptable carrier, and (b) uses of such pharmaceutical compositions in manufacturing a medicament in use for treating osteoarthritis.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

DETAILED DESCRIPTION OF THE INVENTION

Figure 1:
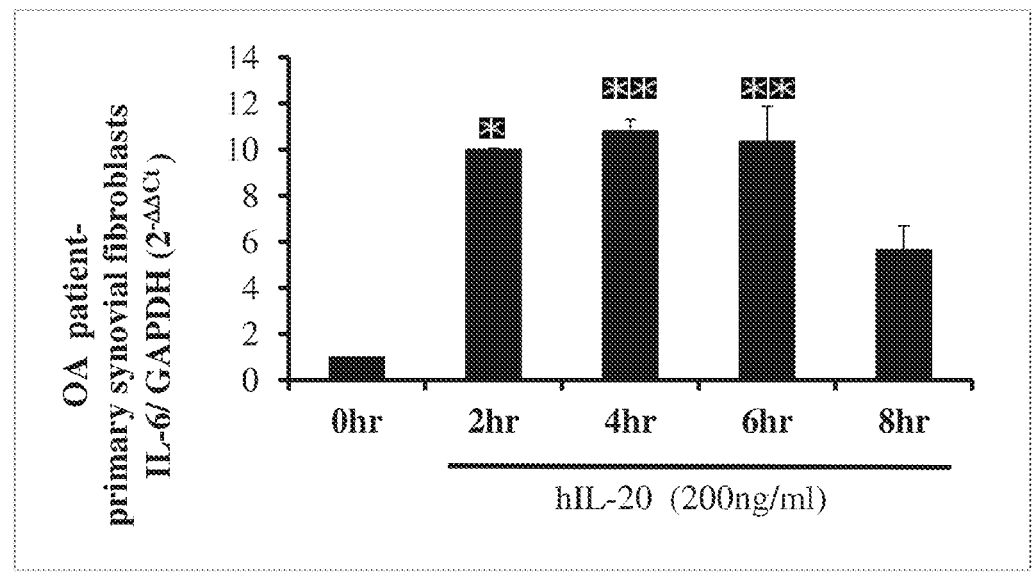
FIG. 1 is a chart showing that IL-20 induced expression of IL-6 (A) and MCP-1 (B) in synovial fibroblasts from osteoarthritis patients. Synovial fibroblasts from osteoarthritis patients were treated with human IL-20 (200 ng/ml). Total RNAs were isolated from the treated cells at various time points as indicated and the expression levels of IL-6 and MCP-1 were analyzed by real-time PCR. *: $p<0.05$; **: $p<0.01$.
Figure 1:
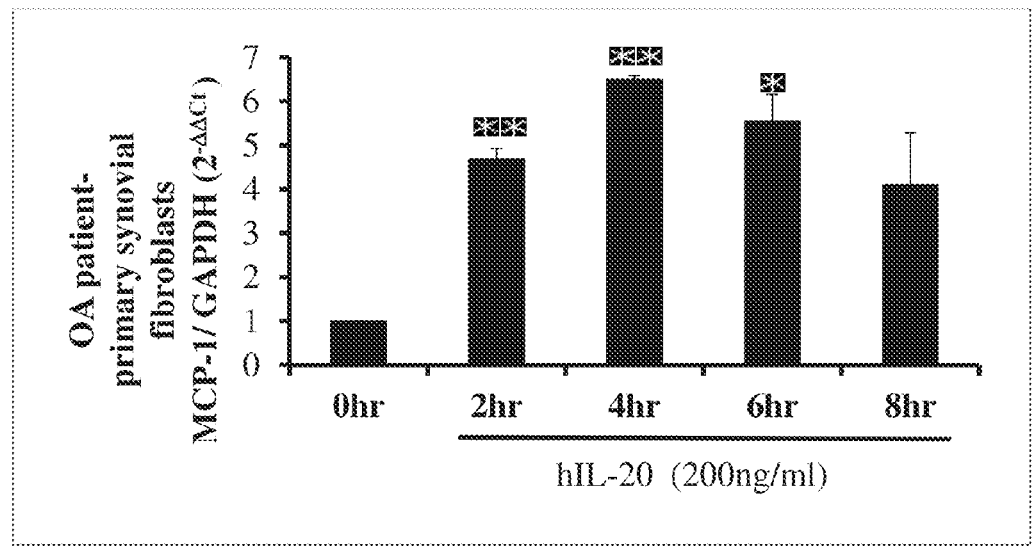

Osteoarthritis (OA) is the most common form of arthritis worldwide and the leading cause of disability in old people. It is a degenerative joint disease characterized by, e.g., cartilage breakdown, formation of bony outgrowths at the joint margin (osteophytes), subchondral bone sclerosis, and alterations to the joint capsule. Sellam et al., Nature Reviews Rheumatology, 2010. 6(11): p. 625-635. Various factors, including age, obesity, sex and joint injury, have been found to be significant risk factors for OA. Roos et al., Nature Reviews Rheumatology, 7(1):57-63, 2010. Currently, clinical therapies for OA included Non-Drug Therapy, Drug Therapy, and Surgical Treatment that help to reduce symptoms and improve tolerance for functional activity, but are only moderately effective and leave patients with substantial pain and a functional burden. Hunter et al., Nature Reviews Rheumatology, 7(1):13-22, 2010.

The present disclosure is based on the unexpected discoveries that IL-20 is involved in the pathogenesis of osteoarthritis and that IL-20 antagonists such as anti-IL-20 antibodies are effective in alleviating osteoarthritis. Accordingly, described herein are methods of treating osteoarthritis using an IL-20 antagonist, e.g., an anti-IL-20 antibody, and pharmaceutical compositions or kits containing such for use in treating osteoarthritis.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

IL-20 Antagonists and Pharmaceutical Compositions Comprising Such

IL-20 is a pro-inflammatory cytokine that belongs to the IL-10 cytokine family. The IL-20 described herein refers to interleukin-20 and variants thereof that retain at least part of the activity of IL-20. As used herein, IL-20 includes all mammalian species of native sequence IL-20, including human, canine, feline, equine, or bovine. In one example, the IL-20 is a human IL-20 (GenBank accession no. NP_061194.2).

IL-20 activates the IL-20 signaling pathway via binding to IL-20 receptor, which is a dimeric complex contains subunits IL-20R1 and IL-20R2 (also known as RA and RB). Such an IL-20 receptor is shared by three functionally different cytokines, i.e., IL-19, IL-20, and IL-24, suggesting that this receptor mediates different signaling pathways dependent upon its binding to a specific cytokine. IL-20 is also capable of binding to a dimeric complex containing IL-20R2 and IL-22R1. The IL-20 receptor disclosed herein refers to one or more polypeptides that are capable of binding to and being activated by IL-20. IL-20 receptors disclosed herein include IL-20R1, IL-20R2 and IL-22R1 of any mammalian species, including, but are not limited to, human, canine, feline, equine, primate, or bovine. Examples of human IL-20 receptors include hIL-20R1 (GenBank Accession No. NM_014432.2), hIL-20R2 (GenBank Accession No. NM_144717.2) and hIL-22R1 (NM_181309.1). Sequences of human IL receptors have been described; for example, in U.S. Pat. Nos. 6,610,286; 7,122,632; 7,393,684; and 7,537,761; and U.S. Pat. App. Pub. Nos. 2006/0263850 A1; 2006/0263851 A1; 2008/0247945 A1, and 2009/0074661 A1.

The IL-20 antagonist to be used in the methods described herein is a molecule that blocks, suppresses, or reduces (including significantly) the biological activity of IL-20, including downstream pathways mediated by IL-20 signaling, such as receptor binding and/or elicitation of a cellular response to IL-20. See US2011/0064731, which is incorporated by reference herein in its entirety. The term "antagonist" implies no specific mechanism of biological action whatsoever, and is deemed to expressly include and encompass all possible pharmacological, physiological, and biochemical interactions with IL-20 whether direct or indirect. For purpose of the present disclosure, it will be explicitly understood that the term "antagonist" encompass all the previously identified terms, titles, and functional states and characteristics whereby the IL-20 itself (e.g., human IL-20), an IL-20 biological activity (including but not limited to its ability to mediate any aspect of osteoarthritis), or the consequences of the biological activity, are substantially nullified, decreased, or neutralized in any meaningful degree, e.g., by at least 20%, 50%, 70%, 85%, 90%, 100%, 150%, 200%, 300%, or 500%, or by 10-fold, 20-fold, 50-fold, 100-fold, 1000-fold, or $10^4$-fold.

Exemplary IL-20 antagonists include, but are not limited to, an anti-IL-20 antibody, an anti-sense nucleic acid molecule directed to an IL-20 (including an anti-sense nucleic acid directed to a nucleic acid encoding IL-20), a small interfering RNA (siRNA) directed toward an IL-20 nucleic acid, a microRNA directed toward an IL-20 nucleic acid, an IL-20 inhibitory compound, an anti-IL-20R antibody (e.g., an antibody specifically binds IL-20R1, IL-20R2, or the dimeric complex formed thereby), an antisense nucleic acid molecule directed to a subunit of an IL-20 receptor, an siRNA or a microRNA directed to a nucleic acid encoding a subunit of an IL-20 receptor, or an IL-20R inhibitory compound. In some embodiments, an IL-20 antagonist binds IL-20 or IL-20 receptor and prevents the formation of IL-20-IL-20R complex, thereby inhibiting the IL-20 signaling pathway. In other embodiments, an IL-20 antagonist inhibits or reduces IL-20 synthesis and/or production (release). Such antagonists include antisense molecules, siRNAs and microRNAs.

Antibodies Capable of Inhibiting the IL-20 Signaling Pathway

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some examples, the antibody disclosed herein specifically binds a target antigen, such as human IL-20 or one of the two subunits of a human IL-20 receptor (e.g., IL-20R1). An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to an IL-20 epitope is an antibody that binds this IL-20 epitope with greater affinity, avidity, more readily, and/or with greater duration than it binds to other IL-20 epitopes or non-IL-20 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

Antibodies capable of inhibiting the IL-20 signaling pathway can be an antibody that binds an IL-20 (e.g., a human IL-20) and inhibits IL-20 biological activity and/or downstream pathways mediated by IL-20. Alternatively, such antibodies can be antibodies that bind an IL-20 receptor (IL-20R), e.g., bind to one or both of the subunits of the IL-20 receptor, and suppress the downstream signaling pathways mediated by the receptor triggered by IL-20.

(i) Anti-IL-20 Antibodies

An anti-IL-20 antibody is an antibody capable of binding to IL-20 and inhibits IL-20 biological activity and/or downstream pathway(s) mediated by IL-20 signaling. In some examples, an anti-IL-20 antibody used in the methods described herein suppresses the IL-20 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold. Examples of anti-IL-20 antibodies include, but are not limited to, those disclosed in U.S. Pat. Nos. 7,435,800; 7,115,714; 7,119,175; 7,151,166; and 7,393,684; and PCT publications WO 2007/081465; WO 99/27103; WO 2004/085475; and WO 2005052000.

The binding affinity of an anti-IL-20 antibody to IL-20 (such as human IL-20) can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$.

One way of determining binding affinity of antibodies to IL-20 is by measuring binding affinity of monofunctional Fab fragments of the antibody. To obtain monofunctional Fab fragments, an antibody (for example, IgG) can be cleaved with papain or expressed recombinantly. The affinity of an anti-IL-20 Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human IL-20, and does not significantly bind an IL-20 from another mammalian species. In some embodiments, the antibody binds human IL-20 as well as one or more IL-20 from another mammalian species. In still other embodiments, the antibody binds IL-20 and does not significantly cross-react with other cytokines (such as the related cytokines IL-10, IL-17A, IL-19, IL-22, IL-24 and IL-26). The epitope(s) bound by the antibody can be continuous or discontinuous.

In some embodiments, the anti-IL-20 antibody described herein is anti-IL-20 antibody 7E, which refers to monoclonal antibody mAb 7E and its functional variants. MAb 7E is produced by the hybridoma cell line deposited at the American Type Culture Collection, 10801 University Boulevard, Manassas, Va. 20110-2209, U.S.A. and assigned a deposit number PTA-8687. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent.

The amino acid sequences and encoding nucleotide sequences of the heavy chain variable region ($V_H$) and light chain variable region ($V_L$) of mAb7E are produced below:

```
Nucleotide sequence (SEQ ID NO: 1) and amino acid sequence
(SEQ ID NO: 2) of mAb 7E heavy chain variable region
gaa ttg aag ctt gag gag tct gga gga ggc ttg gtg cag cct gga   45
 E   L   K   L   E   E   S   G   G   G   L   V   Q   P   G    15 gga tcc atg aaa ctc tct tgt gct gcc tct gga ttc act ttt agt   90
 G   S   M   K   L   S   C   A   A   S   G   F   T   F   S    30 gac gcc tgg atg gac tgg gtc cgc cag tct cca gag aag ggg ctt  135
 D   A   W   M   D   W   V   R   Q   S   P   E   K   G   L    45 gag tgg att gct gaa att aga agc aaa gct aat aat tat gca aca  180
 E   W   I   A   E   I   R   S   K   A   N   N   Y   A   T    60 tac ttt gct gag tct gtg aaa ggg agg ttc acc atc tca aga gat  215
 Y   F   A   E   S   V   K   G   R   F   T   I   S   R   D    75 gat tcc aaa agt ggt gtc tac ctg caa atg aac aac tta aga gct  270
 D   S   K   S   G   V   Y   L   Q   M   N   N   L   R   A    90 gag gac act ggc att tat ttc tgt acc aag tta tca cta cgt tac  315
 E   D   T   G   I   Y   F   C   T   K   L   S   L   R   Y   105 tgg ttc ttc gat gtc tgg ggc gca ggg acc acg gtc acc gtc tcc  360
 W   F   F   D   V   W   G   A   G   T   T   V   T   V   S   120 tca                                                          363
 S                                                           121

Nucleotide sequence (SEQ ID NO: 3) and amino acid sequence
(SEQ ID NO: 4) of mAb 7E light chain variable region
gat ttt gtg atg acc cag act cca ctc act ttg tcg gtt acc att   45
 D   F   V   M   T   Q   T   P   L   T   L   S   V   T   I    15 gga caa cca gcc tcc atc tct tgc aag tca agt cag agc ctc ttg   90
 G   Q   P   A   S   I   S   C   K   S   S   Q   S   L   L    30
```

```
gat agt gat gga aag aca tat ttg aat tgg ttg tta cag agg cca    135
 D   S   D   G   K   T   Y   L   N   W   L   L   Q   R   P     45 ggc cag tct cca aag cac ctc atc tat ctg gtg tct aaa ctg gac    180
 G   Q   S   P   K   H   L   I   Y   L   V   S   K   L   D     60 tct gga gtc cct gac agg ttc act ggc agt gga tca ggg acc gat    215
 S   G   V   P   D   R   F   T   G   S   G   S   G   T   D     75 ttc aca ctg aga atc agc aga gtg gag gct gag gat ttg gga gtt    270
 F   T   L   R   I   S   R   V   E   A   E   D   L   G   V     90 tat tat tgc tgg caa agt aca cat ttt ccg tgg acg ttc ggt gga    315
 Y   Y   C   W   Q   S   T   H   F   P   W   T   F   G   G    105 ggc acc aag ctg gaa atc aaa cgg                                339
 G   T   K   L   E   I   K   R                                 113
```

A functional variant (equivalent) of mAb7E has essentially the same epitope-binding specificity as mAb7E and exhibits at least 20% (e.g., 30%, 40%, 50%, 60%, 70%, 80%, 90%, or greater) of the activity of neutralizing a signaling pathway mediated by IL-20 as relative to mAb7E. In some embodiments, a functional variant of mAb7E contains the same regions/residues responsible for antigen-binding as mAb7E, such as the same specificity-determining residues in the CDRs or the whole CDRs. The regions/residues that are responsible for antigen-binding can be identified from amino acid sequences of the heavy chain/light chain sequences of mAb7GW or mAb51D (shown above) by methods known in the art. See, e.g., www.bioinf.org.uk/abs; Almagro, J. Mol. Recognit. 17:132-143 (2004); and Chothia et al., J. Mol. Biol. 227:799-817 (1987).

In addition, determination of CDR regions in an antibody is well within the skill of the art. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

In some examples, a functional variant of mAb7E comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of mAb7E, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of mAb7E.

Alternatively, the functional variant of mAb7E comprises a $V_H$ chain at least 75% (e.g., 80%, 85%, 90%, 95%, or 98%) identical to the $V_H$ chain (mature or precursor) of mAb7E and a $V_L$ chain at least 75% (e.g., 80%, 85%, 90%, 95%, or 98%) identical to the $V_L$ chain (mature of precursor) of mAb7E.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other examples, a functional variant of mAb7E comprises a $V_H$ chain that includes up to 5 (e.g., 1, 2, 3, 4, or 5) amino acid residue variations in the $V_H$ CDR regions ($V_H$ CDR1, CDR2, and/or CDR3) as compared to the $V_H$ CDRs of mAb7E, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of mAb7E.

Functional variants of mAb7E are also disclosed in U.S. Pat. No. 7,611,705 and US2011/0064731, both of which are incorporated by reference herein.

In one example, a functional variant of mAb7E is a humanized antibody derived from mAb7E. Provided below are exemplary humanized mAb7E antibodies HL1 and HL2; see also U.S. patent application Ser. No. 13/477,476:

```
Amino acid sequence and encoding nucleotide sequence of the V_H chain of humanized
anti-IL-20 antibodies HL1 and HL2:
                ATG TAC TTG GGA CTG AAC TAT GTT TTC ATC GTT TTT CTC CTG AAT
                 M   Y   L   G   L   N   Y   V   F   I   V   F   L   L   N GGT GTC CAG AGT GAA GTG CAG CTT GTG GAG TCT GGA GGA GGC TTG GTG CAG CCT GGA
 G   V   Q   S   E   V   Q   L   V   E   S   G   G   G   L   V   Q   P   G GGA TCC CTG AAA CTC TCT TGT GCT GCC TCT GGA TTC ACT TTT AGT GAC GCC TGG ATG
 G   S   L   K   L   S   C   A   A   S   G   F   T   F   S   D   A   W   M GAC TGG GTC CGC CAG GCT TCC GGG AAG GGG CTT GAG TGG ATT GCT GAA ATT AGA AGC
 D   W   V   R   Q   A   S   G   K   G   L   E   W   I   A   E   I   R   S

AAA GCT AAT AAT TAT GCA ACA TAC TTT GCT GAG TCT GTG AAA GGG AGG TTC ACC ATC
```

```
                                         -continued
K    A    N    N    Y    A    T    Y    F    A    E    S    V    K    G    R    F    T    I TCA  AGA  GAT  GAT  TCC  AAA  AAC  ACC  GCC  TAC  CTG  CAA  ATG  AAC  AGC  TTA  AAA  ACC  GAG
 S    R    D    D    S    K    N    T    A    Y    L    Q    M    N    S    L    K    T    E GAC  ACT  GCC  GTT  TAT  TAC  TGT  ACC  AAG  TTA  TCA  CTG  CGT  TAC  TGG  TTC  TTC  GAT  GTC
 D    T    A    V    Y    Y    C    T    K    L    S    L    R    Y    W    F    F    D    V TGG  GGC  CAG  GGG  ACC  CTG  GTC  ACC  GTC  TCC  TCA  (SEQ ID NO: 5)
 W    G    Q    G    T    L    V    T    V    S    S    (SEQ ID NO: 6)
```

The underlined region refers to the signal peptide and the boldfaced/italic regions are the CDRs. SEQ ID NOs: 7 and 8 represent the mature $V_H$ amino acid sequence (lacking the signal peptide) and its encoding nucleotide sequence, respectively.

```
Amino acid sequence and encoding nucleotide sequence of the V_L chain (VL2) of a
humanized anti-IL-20 antibody HL2:
            ATG  ATG  AGT  CCT  GCC  CAG  TTC  CTG  TTT  CTG  TTG  GTG  CTC  TGG  ATT
             M    M    S    P    A    Q    F    L    F    L    L    V    L    W    I CGG  GAA  ACC  AAC  GGT  GAT  ATC  GTG  ATG  ACC  CAG  ACT  CCA  CTC  TCT  TTG  TCC  GTT
 R    E    T    N    G    D    I    V    M    T    Q    T    P    L    S    L    S    V ACC  CCT  GGA  CAA  CCA  GCC  TCC  ATC  TCT  TGC  AAG  TCA  AGT  CAG  AGC  CTC  TTG  GAT
 T    P    G    Q    P    A    S    I    S    C    K    S    S    Q    S    L    L    D AGT  GAT  GGA  AAG  ACA  TAT  TTG  AAT  TGG  TTG  TTA  CAG  AAG  CCA  GGC  CAG  TCT  CCA
 S    D    G    K    T    Y    L    N    W    L    L    Q    K    P    G    Q    S    P CAG  CAC  CTC  ATC  TAT  CTG  GTG  TCT  AAA  CTG  GAC  TCT  GGA  GTC  CCT  GAC  AGG  TTC
 Q    H    L    I    Y    L    V    S    K    L    D    S    G    V    P    D    R    F AGT  GGC  AGT  GGA  TCA  GGG  ACC  GAT  TTC  ACA  CTG  AAA  ATC  AGC  AGA  GTG  GAG  GCT
 S    G    S    G    S    G    T    D    F    T    L    K    I    S    R    V    E    A GAG  GAT  GTT  GGA  GTT  TAT  TAT  TGC  TGG  CAA  AGT  ACA  CAT  TTT  CCC  TGG  ACC  TTC
 E    D    V    G    V    Y    Y    C    W    Q    S    T    H    F    P    W    T    F GGT  GGA  GGC  ACC  AAG  GTG  GAA  ATC  AAA  (SEQ ID NO: 9)
 G    G    G    T    K    V    E    I    K    (SEQ ID NO: 10)
```

The underlined region refers to the signal peptide and the boldfaced/italic regions are the CDRs. SEQ ID NOs: 11 and 12 represent the mature $V_L$ amino acid sequence (lacking the signal peptide) and its encoding nucleotide sequence, respectively.

Humanized antibody HL1 comprises the same $V_H$ chain as HL2 and a $V_L$ chain that is otherwise identical to the $V_L$ of HL2 except that the I residue at position 2 of mature $V_L$ (SEQ ID NO:13) of HL2 is replaced with F.

Also disclosed herein are functional variants of the above-noted humanized antibodies HL1 and HL2. Such functional variants can comprise a $V_H$ chain that comprises an amino acid sequence at least 85% (e.g., 90%, 92%, 94%, 95%, 96%, 97%, 98%, or 99%) identical to that of the $V_H$ of HL1 and HL2 (precursor or mature form; SEQ ID NO:6 and SEQ ID NO:8, respectively) and a $V_L$ chain that has an amino acid sequence at least 85% (e.g., 90%, 92%, 94%, 95%, 96%, 97%, 98%, or 99%) identical to that of the $V_L$ of HL2 (precursor or mature form; SEQ ID NO:10 and SEQ ID NO:12, respectively). These variants are capable of binding to an IL-20 molecule, particularly a human IL-20 molecule. In some examples, the variants possess similar antigen-binding affinity relative to the exemplary humanized antibody described above (e.g., having a $K_d < 4 \times 10^{-9}$).

(b) Anti-IL-20R Antibodies

An anti-IL-20R antibody is an antibody capable of binding to an IL-20R (e.g., binding specifically to either one of its two subunits or binding to the dimeric complex) and inhibits the biological activity of the IL-20R and/or its downstream pathway(s) mediated by IL-20. In some examples, an anti-IL-20 antibody used in the methods described herein suppresses the IL-20 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold. In some examples, the anti-IL-20R antibody specifically binds IL-20R1, such as human IL-20R1. Such an antibody may have low affinity to IL-20R2 or the IL-20R1/IL-20R2 complex or does not bind IL-20R2 or the IL-20R1/IL-20R2 complex. In other examples, the anti-IL-20R antibody specifically binds IL-20R2, such as human IL-20R2. Such an antibody may have low affinity to IL-20R1 or the IL-20R1/IL-20R2 complex or does not bind IL-20R1 or the IL-20R1/IL-20R2 complex. In yet other examples, the anti-IL-20R antibody described herein specifically binds the IL-20R1/IL-20R2 complex.

The binding affinity of an anti-IL-20R antibody to IL-20R or a subunit thereof (such as human IL-20R or human IL-20R1) can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to IL-20R is by measuring binding affinity of monofunctional Fab fragments of the antibody. To obtain monofunctional Fab fragments, an antibody (for example, IgG) can be cleaved with papain or expressed recombinantly. The affinity of an anti-IL-20R Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human IL-20R or a subunit thereof (e.g., human IL-20R1), and does not significantly bind an IL-20R from another mammalian species. In some embodiments, the antibody binds human IL-20R as well as one or more IL-20R from another mammalian species. In still other embodiments, the antibody binds IL-20R and does not significantly cross-react with other cytokine receptors. The epitope(s) bound by the antibody can be continuous or discontinuous.

In some embodiments, the antibody used in the methods described herein is an antibody having the same heavy chain and light chain variable regions ($V_H$ and $V_L$) as those of monoclonal antibody mAb7GW or mAb51D, the monoclonal antibodies, an antigen-binding fragment thereof, or a functional equivalent of either mAb7GW or mAb51D. Shown below are the amino acid sequences of the heavy chains and light chains of mAb7GW and mAb51D, as well as their encoding nucleotide sequences.

Heavy Chain of mAb7GW:

```
Amino Acid Sequence
                                                              (SEQ ID NO: 14)
M R V L I L L W L F T A F P G I L S V V Q L Q E S G P G L V K P S Q S L S L T C T V T G Y S I
        Signal peptide T S D Y A W N W I R Q F P G N R L E W M G Y I D Y S G S T K Y N P S L K S R I S V T R D
  CDR1                                    CDR2

T S K N Q F F L Q L N S V T T E D T A T Y Y C A R D F G D A Y W G Q G T L V T V S A A K
                                                    CDR3

T T P P S V Y P L A P G S A A Q T N S M V T L G C L V K G Y F P E P V T V T W N S G S L S S G V

H T F P A V L Q S D L Y T L S S S V T V P S S T W P S E T V T C N V A H P A S S T K V D K K I V

P R D C G C K P C I C T V P E V S S V F I F P P K P K D V L T I T L T P K V T C V V V D I S K D

D P E V Q F S W F V D D V E V H T A Q T Q P R E E Q F N S T F R S V S E L P I M H Q D W L N

G K E F K C R V N S A A F P A P I E K T I S K T K G R P K A P Q V Y T I P P P K E Q M A K D K

V S L T C M I T D F F P E D I T V E W Q W N G Q P A E N Y K N T Q P I M D T D G S Y F V Y S K

L N V Q K S N W E A G N T F T C S V L H E G L H N H H T E K S L S H S P G K
(The italic region refers to the heavy chain constant region.)

Nucleotide Sequence
                                                              (SEQ ID NO: 15)
ATGAGAGTGCTGATTCTTTTGTGGCTGTTCACAGCCTTTCCTGGTATCCTGTCTGTTGTGCAGC
     Signal peptide

TTCAGGAGTCGGGACCTGGCCTGGTGAAACCTTCTCAGTCTCTGTCCCTCACCTGCACTG

TCACTGGCTACTCAATCACCAGTGATTATGCCTGGAACTGGATCCGGCAGTTTCCAGGA
                    CDR1

AACAGACTGGAGTGGATGGGCTACATAGACTACAGTGGTAGCACTAAATACAACCCC
                      CDR2

TCTCTCAAAAGTCGAATCTCTGTCACTCGAGACACATCCAAGAACCAGTTCTTCCTGCA

GTTGAATTCTGTGACTACTGAGGACACAGCCACATATTACTGTGCAAGAGACTTTGGTG
                                                    CDR3

ATGCTTACTGGGGCCAGGGGACTCTGGTCACTGTCTCTGCAGCCAAAACGACACCCCCAT

CTGTCTATCCACTGGCCCCTGGATCTGCTGCCCAAACTAACTCCATGGTGACCCTGGGATGCC

TGGTCAAGGGCTATTTCCCTGAGCCAGTGACAGTGACCTGGAACTCTGGATCCCTGTCCAGCG

GTGTGCACACCTTCCCAGCTGTCCTGCAGTCTGACCTCTACACTCTGAGCAGCTCAGTGACTGT

CCCCTCCAGCACCTGGCCCAGCGAGACCGTCACCTGCAACGTTGCCCACCCGGCCAGCAGCA

CCAAGGTGGACAAGAAAGATGTGCCCAGGGATTGTGGTTGTAAGCCTTGCATATGTACAGTCCC

AGAAGTATCATCTGTCTTCATCTTCCCCCCAAAGCCCAAGGATGTGCTCACCATTACTCTGACTC

CTAAGGTCACGTGTGTTGTGGTAGACATCAGCAAGGATGATCCCGAGGTCCAGTTCAGCTGGT

TTGTAGATGATGTGGAGGTGCACACAGCTCAAACGCAACCCCGGGAGGAGCAGTTCAACAGCA

CTTTCCGCTCAGTCAGTGAACTTCCCATCATGCACCAGGACTGGCTCAATGGCAAGGAGTTCAA

ATGCAGGGTCAACAGTGCAGCTTTCCCTGCCCCATCGAGAAAACCATCTCCAAAACCAAAGG

CAGACCGAAGGCTCCACAGGTGTACACCATTCCACCTCCCAAGGAGCAAATGGCCAAGGATAA
```

-continued

AGTCAGTCTGACCTGCATGATAACAGACTTCTTCCCTGAAGACATTACTGTGGAGTGGCAGTGG

AATGGGCAGCCAGCGGAGAACTACAAGAACACTCAGCCCATCATGGACACAGATGGCTCTTAC

TTCGTCTACAGCAAGCTCAATGTGCAGAAGAGCAACTGGGAGGCAGGAAATACTTTCACCTGCT

CTGTGTTACATGAGGGCCTGCACAACCACCATACTGAGAAGAGCCTCTCCCACTCTCCTGGTAA

ATGA (The italic region encodes the heavy chain constant region.)

Light Chain of mAb7GW:

Amino Acid Sequence
(SEQ ID NO: 16)

<u>M D S Q A Q V L M L L L L W V S G S C G</u> D I V M S Q S P S S L A V S V G E K V T M S C K S S
      Signal peptide

Q S L L Y S R N Q K N Y L A W Y Q L K P G Q S P K L L I Y W A S T R E S G V P D R F T G
    CDR1                                                    CDR2

S G S G T D F T L T I S S V K A E D L A V Y Y C Q Q Y Y S Y P L T F G A G T K L E L K R A
                                                             CDR3

*D A A P T V S I F P P S S E Q L T S G G A S V V C F L N N F Y P K D I N V K W K I D G S E R Q N*

*G V L N S W T D Q D S K D S T Y S M S S T L T L T K D E Y E R H N S Y T C E A T H K T S T S P I*

*V K S F N R N E C* (The italic region refers to the light chain constant region.)

Nucleotide Sequence
(SEQ ID NO: 17)

<u>ATGGATTCACAGGCCCAGGTTCTTATGTTACTGCTGCTATGGGTATCTGGTTCCTGTGGGACA</u>
        Signal peptide

TTGTGATGTCACAGTCTCCATCCTCCCTAGCTGTGTCAGTTGGAGAGAAGGTTACTATGA

GCTGCAAGTCCAGTCAGAGCCTTTTATATAGTAGGAATCAAAAGAACTACTTGGCCT
                    CDR1

GGTACCAGCTGAAGCCAGGGCAGTCTCCTAAACTGCTGATTTACTGGGCATCCACTAGG
                                                        CDR2

GAATCTGGGGTCCCTGATCGCTTCACAGGCAGTGGATCTGGGACAGATTTCACTCTCACC

ATCAGCAGTGTGAAGGCTGAAGACCTGGCAGTTTATTACTGTCAGCAATATTATAGCTA
                                                            CDR3

TCCGCTCACGTTCGGTGCTGGGACCAAGCTGGAGCTGAAACGGGCTGATGCTGCACCAAC

*TGTATCCATCTTCCCACCATCCAGTGAGCAGTTAACATCTGGAGGTGCCTCAGTCGTGTGCTTC*

*TTGAACAACTTCTACCCCAAAGACATCAATGTCAAGTGGAAGATTGATGGCAGTGAACGACAAA*

*ATGGCGTCCTGAACAGTTGGACTGATCAGGACAGCAAAGACAGCACCTACAGCATGAGCAGCA*

*CCCTCACGTTGACCAAGGACGAGTATGAACGACATAACAGCTATACCTGTGAGGCCACTCACAA*

*GACATCAACTTCACCCATTGTCAAGAGCTTCAACAGGAATGAGTGTTAG*
(The italic region encodes the light chain constant region.)

Heavy Chain of mAb51D:

Amino Acid Sequence
(SEQ ID NO: 18)
<u>MNFGLSLIFLALILKGVQC</u>EVQLVEAGGDLVKPGGSLKLSCAASGFSLSNYGMSWVRQTPDK
    Signal peptide                                                  CDR1

RLEWVASISSGGRFTSYPDSVRGRFTISRDNAKNTLYLQMSGLKSEDTAMYYCARHDGNG
         CDR2                                                      CDR3

GDYWGQGTSVTVSS*AKTTPPSVYPLAPGSAAQTNSMVTLGCLVKGYFPEPVTVTWNSGSLSSGVH*

*TFPAVLQSDLYTLSSSVTVPSSTWPSETVTCNVAHPASSTKVDKKIVPRDCGCKPCICTVPEVSSVFIF*

*PPKPKDVLTITLTPKVTCVVVDISKDDPEVQFSWFVDDVEVHTAQTQPREEQFNSTFRSVSELPIM*

-continued

*HQDWLNGKEFKCRVNSAAFPAPIEKTISKTKGRPKAPQVYTIPPPKEQMAKDKVSLTCMITDFFPE*

*DITVEWQWNGQPAENYKNTQPIMDTDGSYFVYSKLNVQKSNWEAGNTFTCSVLHEGLHNHHTEK*

*SLSHSPGK*
(The italic region refers to the heavy chain constant region.)

Nucleotide Sequence
(SEQ ID NO: 19)
<u>ATGAACTTCGGGCTCAGCCTGATTTTCCTTGCCCTCATTTTAAAAGGTGTCCAGTGT</u>GAGGTGC
       Signal peptide

AGCTGGTGGAGGCTGGGGGAGACTTAGTGAAGCCTGGAGGGTCCCTGAAACTCTCCTGT

GCGGCCTCTGGATTCAGTTTGAGTAACTATGGCATGTCCTGGGTTCGCCAGACTCCAGA
                     CDR1

CAAGAGGCTGGAGTGGGTCGCAAGCATTAGTAGTGGTGGTCGTTTCACCTCCTATCC
                               CDR2

AGACAGTGTGAGGGGGCGATTCACCATCTCCAGAGACAATGCCAAGAACACCCTGTAC

CTGCAAATGAGCGGTCTGAAGTCTGAGGACACAGCCATGTATTACTGTGCAAGACACGA

CGGCAACGGTGGGGACTACTGGGGTCAAGGAACCTCAGTCACCGTCTCCTCAGCCAAA
   CDR3

*ACGACACCCCCATCTGTCTATCCACTGGCCCCTGGATCTGCTGCCCAAACTAACTCCATGGTGA*

*CCCTGGGATGCCTGGTCAAGGGCTATTTCCCTGAGCCAGTGACAGTGACCTGGAACTCTGGAT*

*CCCTGTCCAGCGGTGTGCACACCTTCCCAGCTGTCCTGCAGTCTGACCTCTACACTCTGAGCA*

*GCTCAGTGACTGTCCCCTCCAGCACCTGGCCCAGCGAGACCGTCACCTGCAACGTTGCCCAC*

*CCGGCCAGCAGCACCAAGGTGGACAAGAAAATTGTGCCCAGGGATTGTGGTTGTAAGCCTTGC*

*ATATGTACAGTCCCAGAAGTATCATCTGTCTTCATCTTCCCCCCAAAGCCCAAGGATGTGCTCA*

*CCATTACTCTGACTCCTAAGGTCACGTGTGTTGTGGTAGACATCAGCAAGGATGATCCCGAGGT*

*CCAGTTCAGCTGGTTTGTAGATGATGTGGAGGTGCACACAGCTCAGACGCAACCCCGGGAGGA*

*GCAGTTCAACAGCACTTTCCGCTCAGTCAGTGAACTTCCCATCATGCACCAGGACTGGCTCAAT*

*GGCAAGGAGTTCAAATGCAGGGTCAACAGTGCAGCTTTCCCTGCCCCCATCGAGAAAACCATC*

*TCCAAAACCAAAGGCAGACCGAAGGCTCCACAGGTGTACACCATTCCACCTCCCAAGGAGCAG*

*ATGGCCAAGGATAAAGTCAGTCTGACCTGCATGATAACAGACTTCTTCCCTGAAGACATTACTG*

*TGGAGTGGCAGTGGAATGGGCAGCCAGCGGAGAACTACAAGAACACTCAGCCCATCATGGAC*

*ACAGATGGCTCTTACTTCGTCTACAGCAAGCTCAATGTGCAGAAGAGCAACTGGGAGGCAGGA*

*AATACTTTCACCTGCTCTGTGTTACATGAGGGCCTGCACAACCACCATACTGAAGAGCCTCT*

*CCCACTCTCCTGGTAAATGA*
(The italic region encodes the heavy chain constant region.)

Light Chain of mAb51D:

Amino Acid Sequence
(SEQ ID NO: 20)
<u>MDFQVQIFSFLLISASVIMSRGQ</u>IVLSQFPAILSASPGEKVTMTCRARSSVSFMHWYQQKPGS
    Signal peptide                                       CDR1

SPKPWIYATSNLASGVPPRFSGSGSGTSYSLTISRVEAEDAATYYCQQWSSNPYTFGGGTKLE
     CDR2                                               CDR3

*IKRADAAPTVSIFPPSSEQLTSGGASVVCFLNNFYPKDINVKWKIDGSERQNGVLNSWTDQDSKDST*

*YSMSSTLTLTKDEYERHNSYTCEATHKTSTSPIVKSFNRNEC*
(The italic region refers to the light chain constant region)

Nucleotide Sequence
(SEQ ID NO: 21)
<u>ATGGATTTTCAAGTGCAGATTTTCAGCTTCCTGCTAATCAGTGCTTCAGTCATAATGTCCA</u>

-continued
Signal peptide

GAGGACAAATTGTTCTCTCCCAGTTTCCAGCAATCCTGTCTGCATCTCCAGGGGAGAAGG

TCACAATGACTTGCAGGGCCAGGTCAAGTGTAAGTTTCATGCACTGGTACCAGCAGAA
　　　　　　　　　　　　　　CDR1

GCCAGGATCCTCCCCCAAACCCTGGATTTATGCCACATCCAACCTGGCTTCTGGAGTCC
　　　　　　　　　　　　　　　　　　　　　　　　CDR2

CTCCTCGCTTCAGTGGCAGTGGGTCTGGGACCTCTTACTCTCTCACAATCAGCAGAGTGG

AGGCTGAAGATGCTGCCACTTATTACTGCCAGCAGTGGAGTAGTAACCCATACACGTTC
　　　　　　　　　　　　　　　　　　　　　CDR3

GGAGGGGGGACTAAGCTGGAAATAAAACGGGCTGATGCTGCACCAACTGTATCCATCTTCC

*CACCATCCAGTGAGCAGTTAACATCTGGAGGTGCCTCAGTCGTGTGCTTCTTGAACAACTTCTA*

*CCCCAAAGACATCAATGTCAAGTGGAAGATTGATGGCAGTGAACGACAAAATGGCGTCCTGAA*

*CAGTTGGACTGATCAGGACAGCAAAGACAGCACCTACAGCATGAGCAGCACCCTCACGTTGAC*

*CAAGGACGAGTATGAACGACATAACAGCTATACCTGTGAGGCCACTCACAAGACATCAACTTCA*

*CCCATTGTCAAGAGCTTCAACAGGAATGAGTGTTAG* (The italic region encodes the light chain constant region.)

A functional equivalent of mAb7GW or mAb51D has the same epitope-binding specificity as mAb7GW or mAb51D and exhibits at least 20% (e.g., 30%, 40%, 50%, 60%, 70%, 80%, 90%, or greater) of the activity of neutralizing a signaling pathway mediated by IL-20R1 as relative to mAb7GW or mAb51D. In some embodiments, a functional equivalent of mAb7GW or mAb51D contains the same regions/residues responsible for antigen-binding as mAb7GW or mAb51D, such as the same specificity-determining residues in the CDRs or the whole CDRs. The regions/residues that are responsible for antigen-binding can be identified from amino acid sequences of the heavy chain/light chain sequences of mAb7GW or mAb51D (shown above) by methods known in the art. See, e.g., www.bioinf.org.uk/abs; Almagro, J. Mol. Recognit. 17:132-143 (2004); and Chothia et al., J. Mol. Biol. 227:799-817 (1987).

In some examples, a functional equivalent (variant) of mAb7GW or mAb51D comprises a $V_H$ chain that includes a $V_H$CDR1, $V_H$CDR2, and $V_H$CDR3 at least 75% (e.g., 80%, 85%, 90%, 95%, or 98%) identical to the corresponding $V_H$ CDRs of mAb7GW or mAb51D, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of mAb7GW or mAb51D.

Alternatively, the functional equivalent of mAb7GW or mAb51D comprises a $V_H$ chain at least 75% (e.g., 80%, 85%, 90%, 95%, or 98%) identical to the $V_H$ chain (mature or precursor) of mAb7GW or mAb51D and a $V_L$ chain at least 75% (e.g., 80%, 85%, 90%, 95%, or 98%) identical to the $V_L$ chain (mature of precursor) of mAb7GW or mAb51D.

In other examples, a functional equivalent of mAb7GW or mAb51D comprises a $V_H$ chain that includes up to 5 (e.g., 1, 2, 3, 4, or 5) amino acid residue variations in the $V_H$ CDR regions ($V_H$CDR1, CDR2, and/or CDR3) as compared to the $V_H$ CDRs of mAb7GW or mAb51D, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of mAb7GW or mAb51D.

(c) Antibody Preparation

Antibodies capable of inhibiting the IL-20 signaling pathway as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., human IL-20 or IL-20R1) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-IL-20 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the IL-20 signaling pathway. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the signaling pathway mediated by IL-20. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected. The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to IL-20R1 or IL-20R2 can be identified from the library following routine procedures. Positive clones can be subjected to further screening to identify those that suppress IL-20 receptor activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the IL-20 polypeptide have been replaced (swapped) with sequences from a closely related, but antigenically distinct protein (such as another member of the neurotrophin protein family). By assessing binding of the antibody to the mutant IL-20, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Other IL-20 Antagonists

IL-20 antagonists other than antibodies capable of interfering with the IL-20 signaling pathway as described above can be used in the methods described herein.

In some embodiments of the invention, the IL-20 antagonist comprises at least one antisense nucleic acid molecule capable of blocking or decreasing the expression of a functional IL-20 (e.g., a human IL-20) or a subunit of an IL-20 receptor (e.g., IL-20R1). Nucleotide sequences of the IL-20 and IL-20 receptor subunits are known and are readily available from publicly available databases. See above disclosures. It is routine to prepare antisense oligonucleotide molecules that will specifically bind a target mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-0 sugar modifications well known in the art.

Alternatively, IL-20/IL-20R expression and/or release can be decreased using gene knockdown, morpholino oligonucleotides, small interfering RNA (siRNA or RNAi), microRNA or ribozymes, methods that are well-known in the art. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene. Alternatively, it can be a microRNA.

Optionally, a nucleic acid molecule to be used in the method described herein (e.g., an antisense nucleic acid, a small interfering RNA, or a microRNA) as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim Acta, 1995, 78, 486-504.

In yet another example, the nucleic acid includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

In other embodiments, the IL-20 antagonist comprises at least one IL-20 or IL-20R inhibitory compound. As used herein, "IL-20 inhibitory compound" or "IL-20R inhibitory compound" refers to a compound other than an anti-IL-20 or anti-IL-20R antibody that directly or indirectly reduces, inhibits, neutralizes, or abolishes IL-20/IL-20R biological activity. An IL-20/IL-20R inhibitory compound should exhibit any one or more of the following characteristics: (a) binds to IL-20 or IL-20R and inhibits its biological activity and/or downstream pathways mediated by IL-20 signaling function; (b) prevents, ameliorates, or treats any aspect of osteoarthritis; (c) blocks or decreases IL-20 receptor activation; (d) increases clearance of IL-20 or IL-20R; (e) inhibits (reduces) IL-20 or IL-20R synthesis, production or release. One skilled in the art can prepare other small molecules inhibitory compounds.

In some embodiments, an IL-20 or IL-20R inhibitory compound is an IL-20 mutant, an IL-19 mutant, or an IL-24 mutant, which can bind to an IL-20 receptor but cannot elicit signal transduction. Such a mutant may block binding of wild type IL-20 to an IL-20 receptor thus preventing IL-20 signal transduction.

In other embodiments, the IL-20 or IL-20R inhibitory compounds described herein are small molecules, which can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the IL-20-antagonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The above-mentioned small molecules can be obtained from compound libraries. The libraries can be spatially addressable parallel solid phase or solution phase libraries. See, e.g., Zuckermann et al. J. Med. Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222:301-310, 1991; and U.S. Pat. No. 5,223,409).

In other embodiments, the IL-20 antagonists can be a polypeptide comprising an extracellular portion of an IL-20 receptor (such as IL-20R1, IL-20R2, or IL-22R1), wherein the polypeptide specifically binds to 11-20 and blocks its interaction with one or more IL-20 receptors. In some embodiments, the extracellular portion of the IL-20 receptor is fused to a Fc domain of antibody. Examples of the soluble receptors are described in PCT WO 01/46232.

Identification of IL-20 Antagonists

IL-20 antagonists can be identified or characterized using methods known in the art, whereby reduction, amelioration, or neutralization of an IL-20 biological activity is detected and/or measured. For example, an ELISA-type assay may be suitable for qualitative or quantitative measurement of IL-20 mediated kinase activation by measuring the phosphorylation of proteins activated through an IL-20 cascade. Examples include JNK, ERK, AKT, p38, STAT3 and TRAF6.

The IL-20 antagonists can also be identified by incubating a candidate agent with IL-20 or IL-20R and monitoring any one or more of the following characteristics: (a) binding to IL-20 or IL-20R and inhibiting its biological activity and/or downstream pathways mediated by IL-20 signaling function; (b) preventing, ameliorating, or treating any aspect of osteoarthritis; (c) blocking or decreasing IL-20 receptor activation; (d) increasing clearance of IL-20 or IL-20R; (e) inhibiting (reducing) IL-20 synthesis, production or release. In some embodiments, an IL-20 antagonist is identified by incubating a candidate agent with IL-20 or IL-20R and monitoring binding and attendant reduction or neutralization of a biological activity of IL-20 or IL-20R. The binding assay may be performed with purified IL-20 or IL-20R polypeptide(s), or with cells naturally expressing, or transfected to express, IL-20 or IL-20R polypeptide(s). In one embodiment, the binding assay is a competitive binding assay, where the ability of a candidate antibody to compete with a known IL-20 antagonist for IL-20 or IL-20R binding is evaluated. The assay may be performed in various formats, including the ELISA format. In other embodiments, an IL-20 antagonist is identified by incubating a candidate agent with IL-20 or IL-20R (e.g., IL-20R1) and monitoring attendant inhibition of IL-20R1/IL-20R2 complex formation or IL-20R2/IL-22R1 complex formation. Following initial identification, the activity of a candidate IL-20 antagonist can be further confirmed and refined by bioassays, known to test the targeted biological activities. Alternatively, bioassays can be used to screen candidates directly.

The examples provided below provide a number of assays that can be used to screen candidate IL-20 antagonists. Bioassays include but are not limited to flow cytometry of determine competitive binding of IL-20 to cells in the presence of candidate IL-20 antagonists; and inhibition of IL-20-induced apoptosis in renal epithelial cells. In addition, RT-PCR or Real-time PCR which can be used to directly measure IL-20 expression or to measure expression of genes upregulated by IL-20 such as TNFα MCP-1, IL-1β, IL-6 and VEGF.

Pharmaceutical Compositions

One or more of the above-described IL-20 antagonist can be mixed with a pharmaceutically acceptable carrier (excipient), including buffer, to form a pharmaceutical composition for use in alleviating osteoarthritis. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. In one example, a pharmaceutical composition described herein contains more than one anti-IL-20 or anti-IL-20R antibodies that recognize different epitopes of the target antigen. In another example, the pharmaceutical composition comprises at least two different-typed IL-20 antagonists (e.g., one antibody and one small molecule).

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the IL-20 antagonist (such as an antibody), which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., an IL-20 antagonist) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vnylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing an IL-20 antagonist with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Use of IL-20 Antagonists for Treating Osteoarthritis

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, IL-20 antagonists can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having osteoarthritis, either primary osteoarthritis or secondary osteoarthritis. Primary osteoarthritis includes primary generalized nodal osteoarthritis and erosive osteoarthritis. It is related to but not caused by aging. Secondary osteoarthritis can be caused by various factors, including congenital disorders of joints, diabetes, injuries to joints or ligaments, septic arthritis, ligamentous, Marfan syndrome, obesity, Alkaptonuria, Hemochromatosis and Wilson's disease, Ehlers-Danlos syndrome, inflammatory diseases such as Perthes' disease, Lyme disease, and chronic forms of arthritis. A subject having osteoarthritis can be identified by routine medical examination, e.g., laboratory tests, X-ray examination. A subject suspected of having osteoarthritis might show one or more symptoms of the disorder, e.g., pain, crepitus, muscle spasm and contractions in the tendons, swollen and/or stiff joint. Different from rheumatoid arthritis patients, patients having osteoarthritis usually feel better with gentle use of affected joints but worse with excessive or prolonged use. A subject at risk for osteoarthritis can be a subject having one or more of the risk factors for that disorder. For example, risk factors associated with osteoarthritis include age and/or gender (osteoarthritis occurs in both women and men before age 55 while it occurs more frequently in women after age 55), family history, overweight, occurrence of fractures or other joint injuries, work and leisure factors, and physical deformities.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of osteoarthritis. Alternatively, sustained continuous release formulations of an IL-20 antagonist may be appropriate. Various formulations and devices for achieving sustained release are known in the art.

In one example, dosages for an IL-20 antagonist as described herein may be determined empirically in individuals who have been given one or more administration(s) of IL-20 antagonist. Individuals are given incremental dosages of the antagonist. To assess efficacy of the antagonist, an indicator of osteoarthritis (such as pain, tenderness, stiffness, locking, and/or effusion in one or more joints, such as hand joints including distal interphalangeal joint, carpometacarpal joint, proximal interphalangeal joint, hip, and/or knee) can be followed.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate osteoarthritis, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

When the IL-20 antagonist is not an antibody, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an IL-20 antagonist will depend on the specific IL-20 antagonist(s) (or compositions thereof) employed, the severity of osteoarthritis, whether the antagonist is administered for preventive or therapeutic purposes, previous therapy, the patient's clinical history and response to the antagonist, and the discretion of the attending physician. Typically the clinician will administer an IL-20 antagonist, such as an anti-IL-20 or anti-IL-20R antibody, until a dosage is reached that achieves the desired result. Administration of an IL-20 antagonist can be continuous or intermittent, depending, for example, upon the recipient's physiological condition, whether the purpose of the administration is therapeutic or prophylactic, and other factors known to skilled practitioners. The administration of an IL-20 antagonist (for example if the IL-20 antagonist is an anti-IL-20 antibody) may be essentially continuous over a preselected period of time or may be in a series of spaced dose, e.g., either before, during, or after developing osteoarthritis.

As used herein, the term "treating" refers to the application or administration of a composition including one or more active agents to a subject, who has osteoarthritis, a symptom of osteoarthritis, or a predisposition toward the disease, with the purpose to cure, heal, alleviate, relieve, alter, remedy, ameliorate, improve, or affect the disorder, the symptom of the disease, or the predisposition toward the disease.

Alleviating osteoarthritis includes delaying the development or progression of the disease, or reducing disease severity. Alleviating the disease does not necessarily require curative results. As used therein, "delaying" the development of osteoarthritis means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of Osteoarthritis includes initial onset and/or recurrence.

In some embodiments, the IL-20 antagonist (e.g., an anti-IL-20 antibody or anti-IL-20R antibody such as anti-IL-20R1 antibody) described herein is administered to a subject in need of the treatment at an amount sufficient to reduce the level of the IL-20 receptor/IL-20-mediated signaling by at least 20% (e.g., 30%, 40%, 50%, 60%, 70%, 80%, 90% or greater). In other embodiments, the antagonist is administered in an amount effective in reducing the knee thickness in the subject, and/or reduce the expression level of one or more of proinflammatory factors such as IL-6, MCP-1, IL-1β, and TNFα, of synovial fibroblasts or synovial membrane in the subject.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethylormamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an IL-20 antagonist is administered via site-specific or targeted local delivery techniques. Examples of site-specific or targeted local delivery techniques include various implantable depot sources of the IL-20 antagonist or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

It is also apparent that an expression vector can be used to direct expression of any of the protein-based IL-20 antagonists described herein (e.g., anti-IL-20 antibody, or anti-IL-20R antibody). For example, other IL-20 receptor fragments that are capable of blocking (from partial to complete blocking) IL-20 and/or an IL-20 biological activity are known in the art.

The particular dosage regimen, i.e., dose, timing and repetition, used in the method described herein will depend on the particular subject and that subject's medical history.

In some embodiments, more than one IL-20 antagonist, such as an antibody and a small molecule IL-20 inhibitory compound, may be administered to a subject in need of the treatment. The antagonist can be the same type or different from each other. At least one, at least two, at least three, at least four, at least five different IL-20 antagonists can be co-administered. Generally, those IL-20 antagonists have complementary activities that do not adversely affect each other. IL-20 antagonists can also be used in conjunction with other agents that serve to enhance and/or complement the effectiveness of the agents.

Treatment efficacy can be assessed by methods well-known in the art, e.g., Micro-CT scanning, or monitoring the knee thickness or expression levels of one or more proinflammatory factors such as IL-6 and MCP-1 in the synovial fibroblasts or synovial membrane in a patient subjected to the treatment. See, e.g., Examples 1 and 2 below.

Kits for Use in Alleviating Osteoarthritis

The present disclosure also provides kits for use in alleviating osteoarthritis. Such kits can include one or more containers comprising an IL-20 antagonist (such as an antibody, e.g., mAb7E or its functional variant, mAb7GW or its functional variant, or mAb51D or its functional variant). In some embodiments, the IL-20 antagonist is any antibody capable of inhibiting the IL-20 signaling pathway as described herein. In other embodiments, the kit comprises an IL-20 antagonist that is other than the just-noted antibody.

In some embodiments, the kit can comprise instructions for use in accordance with any of the methods described herein. The included instructions can comprise a description of administration of the IL-20 antagonist to treat, delay the onset, or alleviate osteoarthritis according to any of the methods described herein. The kit may further comprise a description of selecting an individual suitable for treatment based on identifying whether that individual has osteoarthritis. In still other embodiments, the instructions comprise a description of administering an IL-20 antagonist to an individual at risk of osteoarthritis.

The instructions relating to the use of an IL-20 antagonist generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating osteoarthritis. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an IL-20 antagonist, such as an anti-IL-20 antibody.

Kits may optionally provide additional components such as buffers and interpretive information. Normally, the kit comprises a container and a label or package insert(s) on or associated with the container. In some embodiments, the invention provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

Involvement of IL-20 in Osteoarthritis

Materials and Methods
Isolation and Culture of Synovial Fibroblasts and Chondrocytes Freshly isolated synovial tissue obtained from OA Patients was Finely Minced into 2-3-mm pieces and then digested for 1 hour at 37° C. with 0.1% Collagenase (Roche, Mannheim, Germany) in Dulbecco's modified Eagle's medium (DMEM; Gibco BRL, Grand Island, N.Y.). Rheumatoid arthritis (RA) synovial fibroblasts (RASFs) were grown in DMEM containing 10% fetal bovine serum (PBS), All in vitro experiments were performed using primary cultures of RASFs between passages 5 and 10.

Cartilage tissue was digested for 10 min in 0.02% bovine trypsin in phosphate buffered saline (PBS) in the dark and was continuously shaken, at room temperature. The cartilage was then treated for 2 h in 0.02% collagenase type II and in Dulbecco's modified Eagle's medium (DMEM; Gibco BRL, Grand island, NY) at 37° C. The cell suspension was then filtered and the cells collected by centrifugation. The pellet thus harvested was re-suspended with DMEM and seeded with a cell density of $5 \times 10^5$ in a 10 cm culture dish. OA chondrocytes were grown in DMEM contain 1% penicillin-streptomycin with 5% $CO_2$ and 37° C.

Analyzing IL-6 and MCP-1 Expression in Patient OASFs

OA synovial fibroblasts (OMB) were plated for 12 hours in DMEM with 10% FBS. The cells were incubated for 0, 2, 4, 6, and 8 hours with 200 ng/ml of IL-20 to analyze IL-6 and MCP-1 expression. Total RNA was isolated (Invitrogen). Reverse transcription was performed with reverse transcriptase according to the manufacturer's protocol (Clontech). IL-6 and MCP-1 was then amplified on a thermocycler (LC 480; Roche Diagnostics), with SYBR Green (Roche Diagnostics) as the interaction agent. Quantification analysis of messenger RNA (mRNA) was normalized with GAPDH mRNA. Relative multiples of changes in mRNA expression were determined by calculating $2^{-\Delta\Delta Ct}$.

Induction of Rat OA Model and Assessment of Severity

Six-week-old male Sprague-Dawley rats were under general anesthesia with chloral hydrate, the left hind limbs were shaved and prepared for aseptic surgery. Then, the anterior cruciate ligaments (ACL) and the media collateral ligaments (MCL) were transected and the medial menisci (MM) were removed. The contralateral knee joint was sham-operated through the same approach without any ligament transaction or menisectomy. The skin was closed with 3-0 silk sutures. At 3 weeks post-surgery, rats were sacrificed and synovial membrane and cartilage tissue was collected. The fixed knee joints were decalcified and were transected in the frontal plane so the medial and lateral orientation was maintained and both halves were embedded in paraffin. The sections were stained with toluidine blue and evaluated for cartilage damage and osteophyte formation. The cartilage damage was evaluated using the following system: 1=minimal superficial zone only; 2=mild, extends into the upper middle zone; 3=moderate, well into the middle zone; 4=marked into the deep zone but not to tidemark; 5=severe, full thickness degeneration to tidemark. The amount of cartilage damage was assessed as ⅓, ⅔ or 3/3 of the surface of the histological section and the above score was multiplied by 1, 2 or 3, respectively to reflect the extent of the tibial plateau that was involved. Osteophytes were scored 1, 2 or 3 for mild (<40 μm) moderate (40-160 μm) or severe (>160 μM) depending on the size using an ocular micrometer.

Micro-CT scan was also used to evaluate the effects of bone structure and cartilage damage in the rat OA model. Radiologic arthritis severity grades were assessed by a modification of the Kellgren radiologic arthritis criteria as follows:
 Grade 0: normal;
 Grade 1: mild joint space narrowing;
 Grade 2: slight subchondral sclerosis;
 Grade 3: initial osteophyte formation;
 Grade 4: prominent osteophyte formation and small subchondral bone erosion; and
 Grade 5: joint destruction.

Analyzing IL-6 and MCP-1 Expression in Patient OASFs

OASFs were plated for 12 hours in DMEM with 10% FBS. The cells were incubated for 0, 2, 4, 6, and 8 hours with 200 ng/ml of IL-20 to analyze IL-6 and MCP-1 expression. Total RNA was isolated using the kit provided by Invitrogen. Reverse transcription was performed with reverse transcriptase according to the manufacturer's protocol (Clontech), IL-6 and MCP-1 was then amplified on a thermocycler (LC 480; Roche Diagnostics), with SYBR Green (Roche Diagnostics) as the interaction agent. Quantification analysis of mRNA was normalized with GAPDH mRNA. Relative multiples of changes in mRNA expression were determined by calculating $2^{-\Delta\Delta Ct}$.

Analyzing IL-1β, TNF-α, MMP-1 and MMP-13 Expression in Rat OASFs.

Rat OASFs were plated for 12 hours in DMEM with 10% FBS. The cells were incubated for 0, 6, and 8 hours with 200 ng/ml of IL-20 to analyze IL-1β, TNF-α, MMP-1 and MMP-13 expression. Total RNA was isolated using a kit provided by Invitrogen. Reverse transcription was performed with reverse transcriptase according to the manufacturer's protocol (Clontech). IL-1β, TNF-α, MMP-1 and MMP-13 were then amplified on a thermocycler (LC 480; Roche Diagnostics), with SYBR Green (Roche Diagnostics) as the interaction agent. Quantification analysis of mRNA was normalized with GAPDH mRNA. Relative multiples of changes in mRNA expression were determined by calculating $2^{-\Delta\Delta Ct}$.

Results

IL-20 Induced IL-6 and MCP-1 Expression in Patient OASFs

It was reported that the levels of proinflammatory cytokines, including IL-1β, TNF-α and IL-6 are elevated in OA. Hunter, D. J., Nature Reviews Rheumatology, 2010. 7(1): p. 13-22). To investigate the role of IL-20 in that network, OASFs were treated with human IL-20, and the total RNA was collected and reverse transcribed. The mRNA levels of MCP-1, IL-6, and TNF-α in OASFs increased after treatment with human IL-20. FIG. 1.

IL-20 Induced IL-1β, TNT-α, MMP-1 and MMP-13 Expression in Rat OASFs

Figure 2:
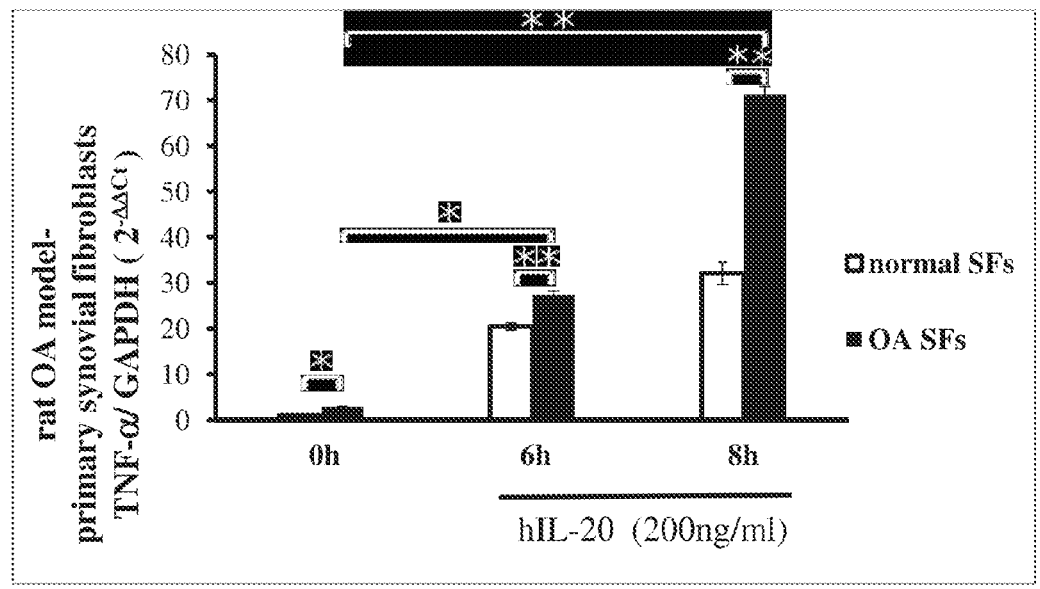
FIG. 2 is a chart showing that IL-20 induced TNFα (A) and IL-1β (B) expression in synovial fibroblasts from rats having surgically induced osteoarthritis. Synovial fibroblasts from OA rats were treated with human IL-20 (200 ng/ml). Total RNAs were isolated from the treated cells at various time points as indicated and the expression levels of TNFα and IL-1β were analyzed by real-time PCR. *: $p<0.05$; **: $p<0.01$.
Figure 2:
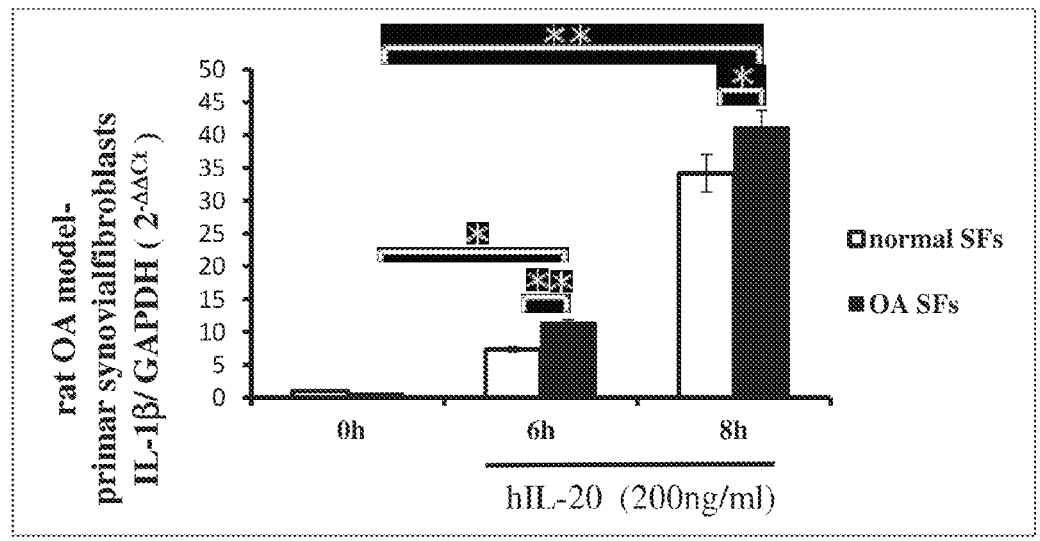
Figure 3:
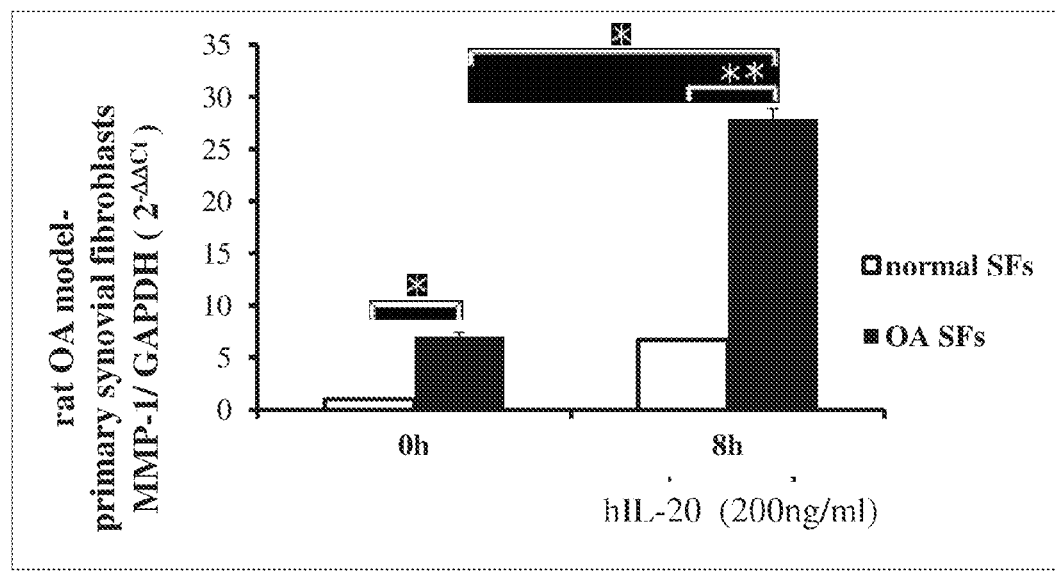
FIG. 3 is a chart showing that IL-20 induced overexpression of MMP-1 (A) and MMP-13 (B) in synovial fibroblasts from rats having surgically induced osteoarthritis. Synovial fibroblasts from OA rats were treated with human IL-20 (200 ng/ml). Total RNAs were isolated from the treated cells at various time points as indicated and the expression levels of MMP-1 and MMP-13 were analyzed by real-time PCR. *: $p<0.05$; **: $p<0.01$.
Figure 3:
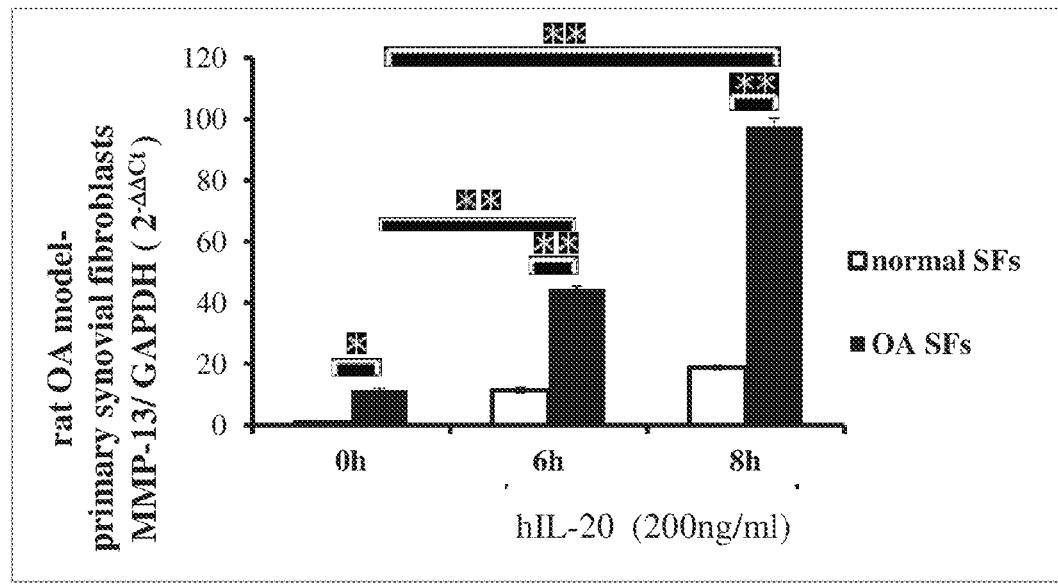

The cytokines such as IL-1β and TNF-α also play a key role in cartilage de-generation in OA, and the MMP family members are the major enzymes that degrade the extracellular matrix of cartilage. Hsu, Y.-H., et. al., Arthritis & Rheumatism, 2010. 62(11): p. 3311-3321. To investigate the role of IL-20 in that network, OASFs from OA rats were treated with human IL-20. The total RNAs were isolated from the treated cells and the mRNA levels of IL-1β, TNF-α, MMP-1 and MMP-13 were analyzed by RT-PCR. As shown in FIGS. 2 and 3, the mRNA levels of IL-1β, TNF-α, MMP-1 and MMP-13 in OASFs increased after treatment with human IL-20 (FIGS. 2 and 3). Additionally, OASFs had higher levels of expression of those cytokines than the healthy SFs.

The above results demonstrate that IL-20 is involved in OA pathogenesis, indicating that agents that inhibit the signaling pathway triggered by IL-20 would be effective in alleviating osteoarthritis.

Example 2

Protective Effects of Anti-IL-20 Antibody in a Surgically-Induced Osteoarthritis Rat Model Materials and Methods Animal Models and IL-20 Antibody (mAb7E) Treatment Male Sprague-Dawley rats (275-300 g; Charles River Breeding Laboratories, Tokyo, Japan) were used in this study. Two or three rats per cage were housed under a specific pathogen-free condition (controlled temperature of 24±3° C. and humidity of 55±15%). Osteoarthritis (OA) was surgically induced in the knee joint of each rat as follows. Each rat was anesthetized with halothane, and after being shaved and disinfected, the left knee joint was exposed through a medial parapatellar approach. The patella was dislocated laterally and the knee placed in full flexion, followed by anterior cruciate and medial collateral ligament transection and medial meniscus resection (ACLT+MMx) with micro-scissors. Hayami T, et. al., Bone. 2006; 38(2):234-43. After the surgery, the joint surface was washed with sterile saline, and both capsule and skin were sutured using Vicryl 4-0 absorbable suture and monofilament 4-0 Nylon threads, respectively.

After the ACLT+MMx surgery described above, rats were divided into 2 groups: group 1 was treated with a control mouse IgG (n=6) while group 2 was treated with anti-IL-20 antibody mAb7E (n=6). After the surgery, each rat received intra-peritoneal (IP) injection of the mIgG control antibody or mAb7E (3 mg/kg) once every 3 days for eight weeks.

Micro-CT Scan and Radiological Evaluation of the Severity of OA

After the rats were scarified, the left lower limb of each rat was isolated for 18 μm isotrophic voxel resolution scans at the tibiofemoral joints using a micro-CT (SkyScan 1076; SkyScan, Aartselaar, Axial, sagittal and coronal images were reconstructed from scanned data, and were reviewed by two orthopedic surgeon using a micro-CT viewer program (DataViewer; SkyScan, Aartselaar, Belgium). Radiologic arthritis severity grades were scored by blinded consensus between two orthopedic surgeons using a modified Kellgren radiologic arthritis criteria described above. See also Saal, A, et. al., Rheumatol Int. 2005; 25(3):161-8.

Tissue Preparation and Histopathological Evaluation

After micro-CT examination, the left lower limb was carefully dissected with preservation of entire femorotibial joint, fixed in 10% phosphate buffered formalin, decalcified in formic acid (Immunocal, Decal Corporation, Tallman, N.Y.), bisected in the frontal plane, and routinely processed into paraffin-embedded blocks. Three step sections from each specimen were stained with toluidine blue. Damage to the articular cartilage and osteophyte size were scored as previously described with the modification that osteophyte size was scored as 0-4 (no osteophyte, <200, <300, <400, >400 μm) (Wancket, L M, et. al., Toxicol Pathol. 2005; 33(4):484-9). The histology scores were assessed by one orthopedic surgeons, blinded to the radiologic results and group label.

Statistical Analysis

Differences in histology, osteophyte score, and radiologic grade between groups were analyzed using a Mann-Whitney U test due to the relatively small number. Data were analyzed using SPSS for Windows 16.0.

Results

Figure 4:
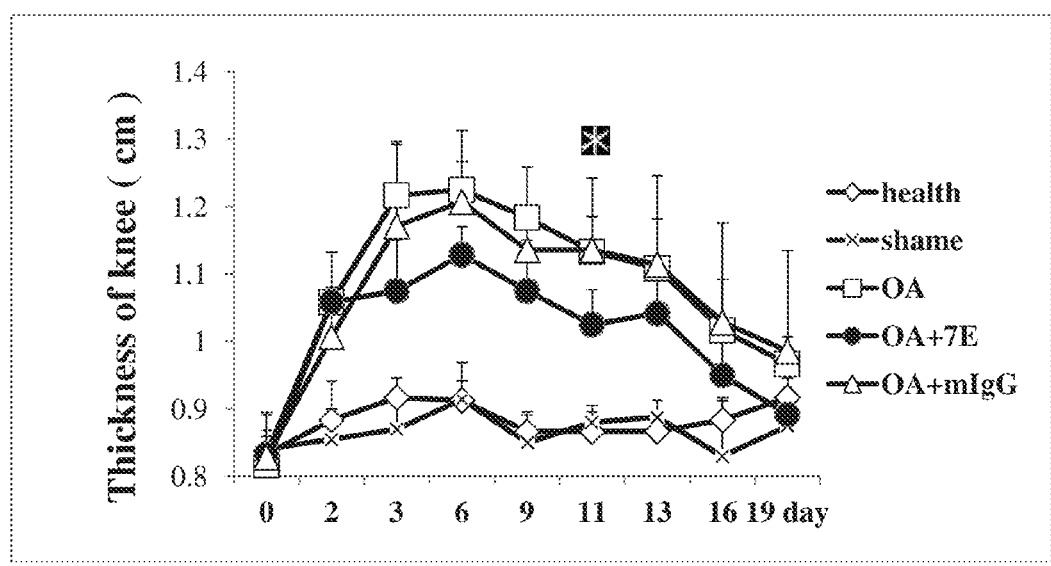
FIG. 4 shows that anti-IL-20 antibody mAb7E reduced thickness of knee joints in rats having surgically induced osteoarthritis (OA rats). The knee thickness, serving as an indicator of OA severity, was examined in five groups of rats: Health rats (n=3), Shame control rats (n=5), OA rats (n=6), mAb7E-treated OA rats (n=6), and control mIgG-treated rats (n=7). OA rats were treated with mAb7E two days after surgery at a dosage of 3 mg/kg, once every three days, for 4 weeks. A: Knee thickness of rats in different groups at various time points. B: Statistical analysis showing that the difference in knee thickness between mAb7E-treated OA rats and control mIgG-treated rats is statistically significant. *: p<0.05.
Figure 4:
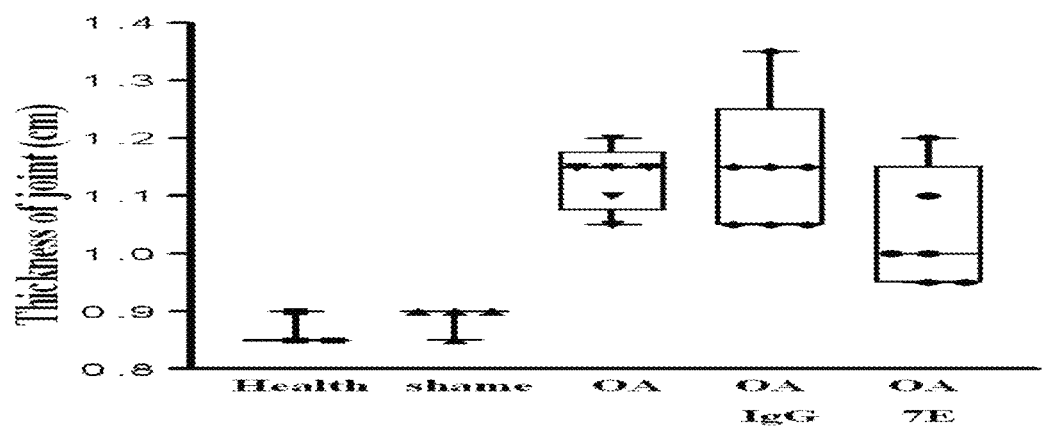
Figure 5:
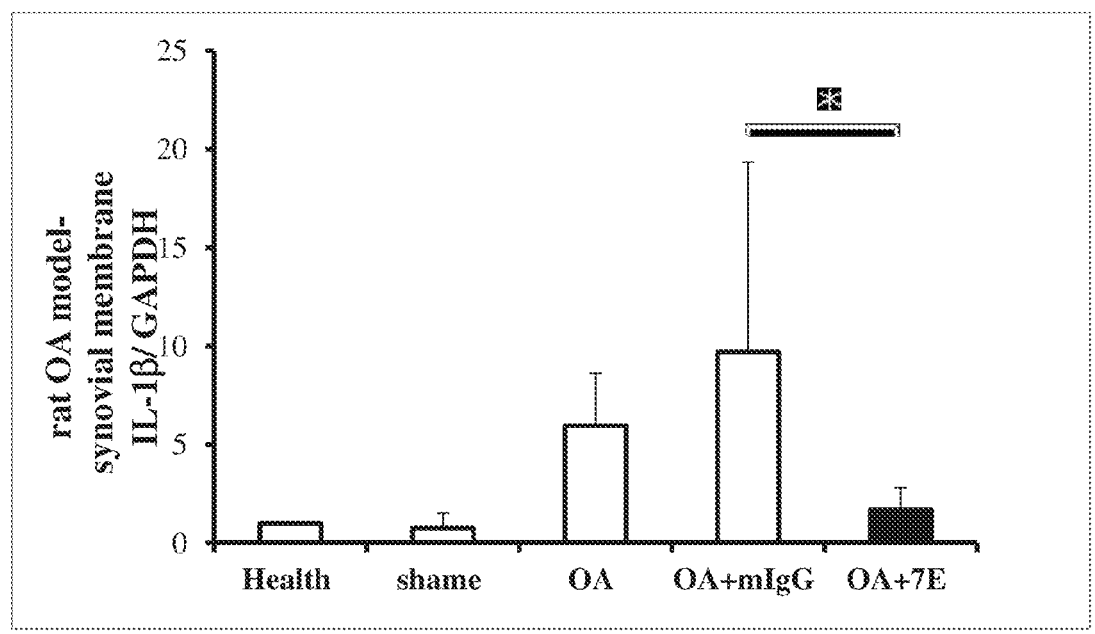
FIG. 5 shows that anti-IL-20 antibody mAb7E reduced IL-1β expression in Synovial fibroblasts from OA rats. Rats were sacrificed 30 days after surgery. The synovial fibroblasts were harvested and total RNAs were isolated. The expression level of IL-1β was determined by real-time PCR. *: p<0.05.

Anti-IL-20 Antibody mAb7E Reduced Thickness of Knee Joints and Decreased IL-1β Expression in OA Synovial Membranes To further confirm the involvement of IL-20 in OA development in vivo, an anti-IL-20 antibody (mAb7E) was used. The mAb7E antibody reduced the thickness of knee joints in OA rats. FIG. 4. Real-time PCR was performed and showed that 7E treatment lowered the expression of IL-1β compared to the control after 4 weeks of in vivo treatment. FIG. 5.

mAb7E Decreased Subchondral Cyst Formation

Figure 6:
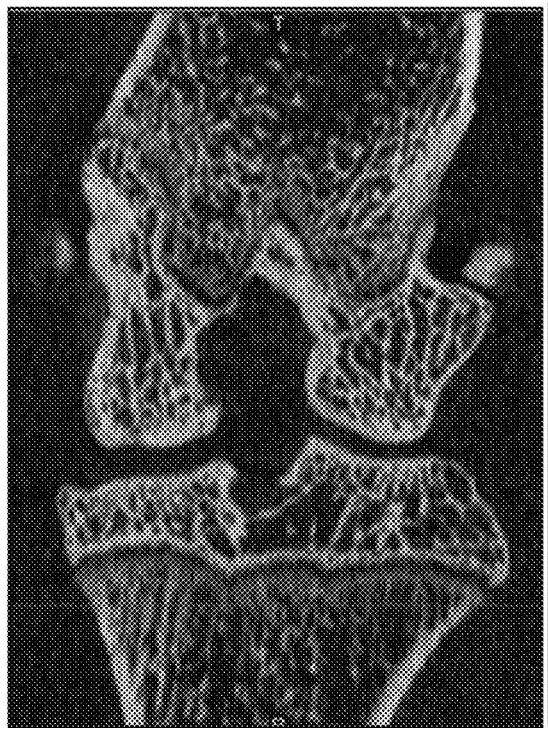
FIG. 6 shows that anti-IL-20 antibody mAb7E reduced subchondral cyst formation in rats having surgically induced osteoarthritis. OA rats were treated with mAb7E or a control mIgG one day after surgery at a dosage of 3 mg/kg, once every three days, for 8 weeks. The rats were sacrificed 57 days after the surgery and examined using Micro-CT scan. The levels of knee joint destruction were determined following the modified K-L grading system as described herein.
Figure 6:
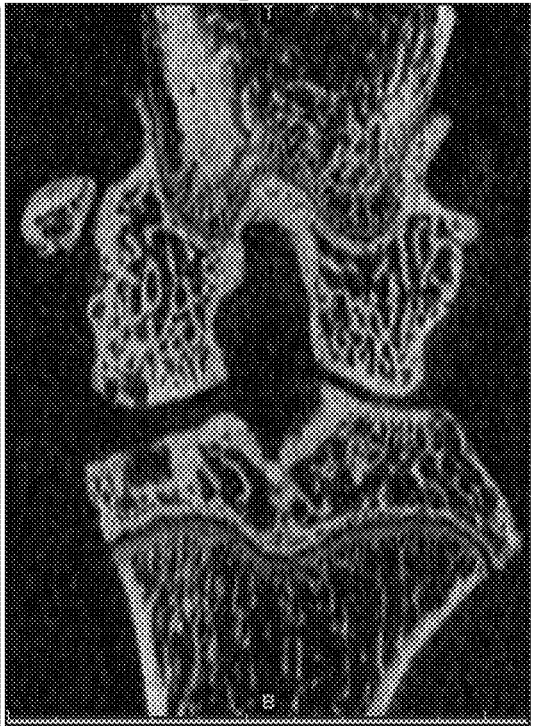

Following 8 weeks of treatment, the modified K-L grades of the group of rats treated with mAb7E were also lower than those of the rats treated with the mIgG control antibody. Micro-computed tomography (Micro-CT) scans of the rat knee showed slight tibial and femoral articular bone erosion defect in the group treated with mAb7E. By contrast, a significant subchondral cyst formation of tibial and femoral articular cartilage was observed in the rat group treated with the mIgG control antibody. FIG. 6.

These in vivo results demonstrated that anti-IL-20 antibodies such as mAb7E have therapeutic potentials in treating OA. Anti-IL-20 (7E) Antibody Treatment Had a Protective Effect on Rats with Surgically-Induced Osteoarthritis.

Figure 7:
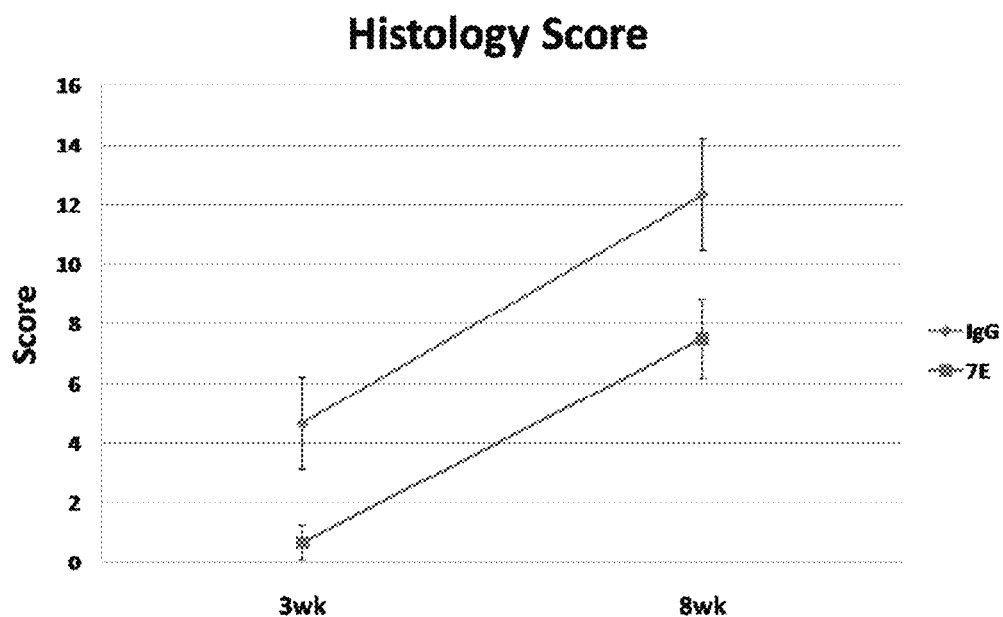
FIG. 7 shows the histology scores (A), osteophyte scores (B), and radiological grades (C) of OA rats treated with mAb7E or a control mIgG antibody.
Figure 7:
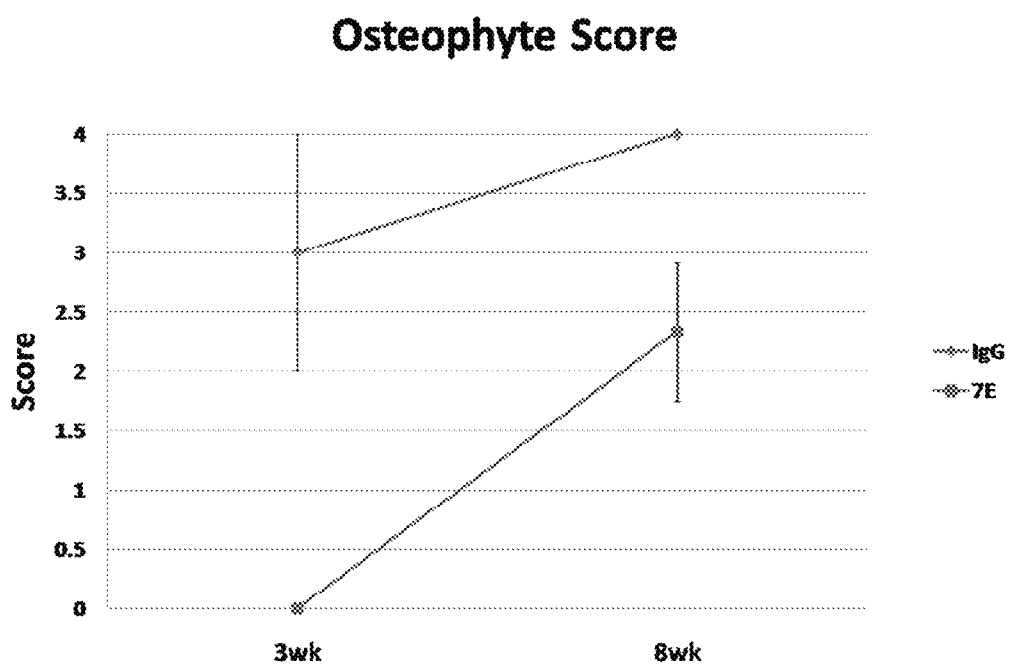
Figure 7:
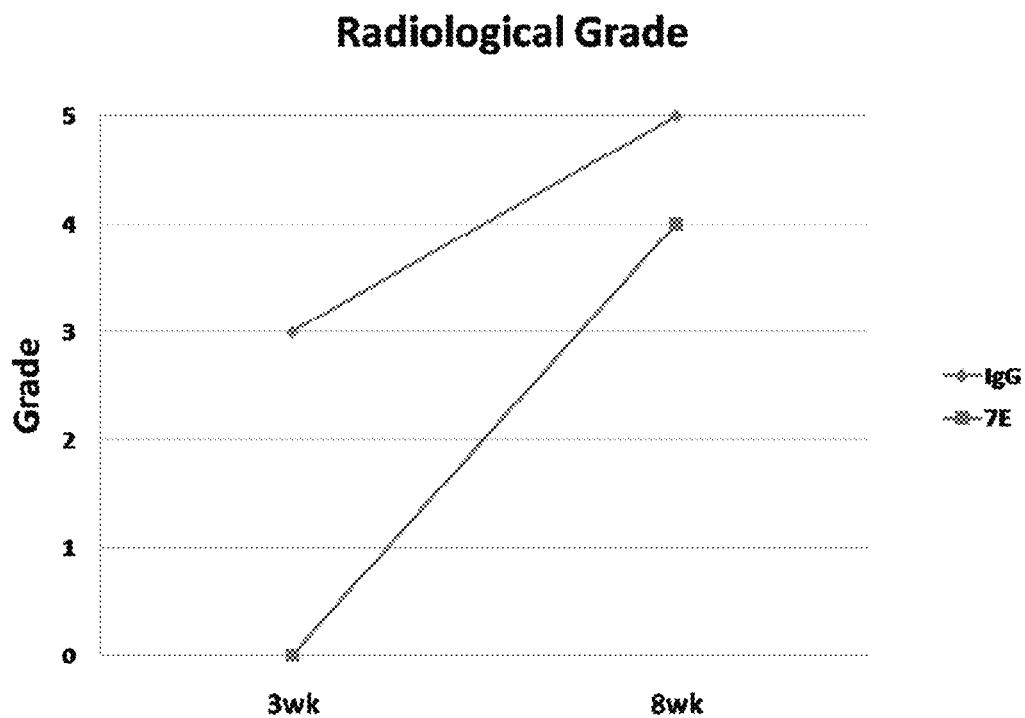

Histological analysis revealed that the rats treated with the control mIgG antibody displayed ACLT+MMx-induced osteoarthritis, which progressed over time. FIG. 7A. To the contrary, the rats treated with mAb7E developed OA in a much less severity as compared to that in the rats treated with the control antibody at the same time point. FIG. 7A. The osteophyte score of the rats treated with mAb7E also reflected less activity of cartilage proliferation in response to surgery-induced instability. FIG. 7B. Notably, at the initial time point (3 weeks post-surgery), the mIgG group displayed the obvious osteophyte formation while the 7E group showed no osteophyte formation.

Similar to the histology results, the radiologic grade increased over time in the control group, while the mAb7E group showed significantly better radiologic grade at the same time point as compared to the control group. FIG. 7C. Likewise, occurrence of osteoarthritis was not observed in the 7E group at the initial time point (3 weeks post-surgery), which is consistent with the histopathological findings.

The above results show that anti-IL-20 (7E) treatment in rats having surgically-induced osteoarthritis had a significant protective effect in delaying progression of the condition as compared to a group treated with a control antibody. This data indicates that IL-antagonists, such as anti-IL-20 antibodies, would be effective in treating osteoarthritis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for alleviating osteoarthritis in a subject, comprising administering to a subject in need thereof an effective amount of an antibody that inhibits a signaling pathway mediated by IL-20, wherein the antibody is selected from the group consisting of:
   (i) a humanized antibody comprising a heavy chain variable region ($V_H$), which comprises the amino acid sequence of SEQ ID NO:7, and a light chain variable region ($V_L$), which comprises the amino acid sequence of SEQ ID NO:11;
   (ii) a humanized antibody comprising a $V_H$, which comprises the amino acid sequence of SEQ ID NO:7, and a $V_L$, which comprises the amino acid sequence of SEQ ID NO:13;
   (iii) an antibody comprising the same complementary determining regions (CDRs) as monoclonal antibody mAb51D, and
   (iv) an antibody comprising the same CDRs as monoclonal antibody mAb7GW.

2. The method of claim 1, wherein the antibody is a full-length antibody or an antigen-binding fragment thereof.

3. The method of claim 1, wherein the antibody is a human antibody, a humanized antibody, a chimeric antibody, or a single-chain antibody.

4. The method of claim 1, wherein the antibody is (i) or (ii).

5. The method of claim 4, wherein the antibody is a full-length antibody or an antigen-binding fragment thereof.

6. The method of claim 1, wherein the antibody is (iii) or (iv).

7. The method of claim 6, wherein the antibody comprises the same $V_H$ and $V_L$ chains as mAb51D or mAb7GW.

8. The method of claim 7, wherein the antibody is a full-length antibody or an antigen-binding fragment thereof.

9. The method of claim 7, wherein the antibody is a human antibody, a humanized antibody, a chimeric antibody, or a single-chain antibody.

10. The method of claim 6, wherein the antibody is a humanized antibody of mAb51D or mAb7GW.

11. The method of claim 1, wherein the subject is a human patient having or being suspected of having osteoarthritis.

12. The method of claim 11, wherein the human patient is 45 or older.

13. The method of claim 12, wherein the human patient is 65 or older.

* * * * *